(12) United States Patent
Woehrmann et al.

(10) Patent No.: US 8,343,467 B2
(45) Date of Patent: Jan. 1, 2013

(54) GLYCOPYRROLATE IN COSMETIC PREPARATIONS

(75) Inventors: Michael Woehrmann, Hamburg (DE); Lara Terstegen, Hamburg (DE); Stefan Biel, Hamburg (DE); Thomas Raschke, Pinneberg (DE); Svenja-Kathrin Cerv, Hamburg (DE); Werner Zilz, Halstenbek (DE); Sven Untiedt, Hamburg (DE); Thomas Nuebel, Hamburg (DE); Uwe Schoenrock, Nahe (DE); Heiner Max, Hamburg (DE); Helga Biergiesser, Reinbek (DE); Yvonne Eckhard, Hamburg (DE); Heike Miertsch, Hamburg (DE); Heike Foelster, Hamburg (DE); Cornelia Meier-Zimmerer, Nuremberg (DE); Bernd Traupe, Kaltenkirchen (DE); Inge Kruse, Hamburg (DE)

(73) Assignee: Beiersdorf AG, Hamburg (DE)

( * ) Notice: Subject to any disclaimer, the term of this patent is extended or adjusted under 35 U.S.C. 154(b) by 542 days.

(21) Appl. No.: 11/722,992

(22) PCT Filed: Dec. 27, 2005

(86) PCT No.: PCT/EP2005/057186
§ 371 (c)(1),
(2), (4) Date: Jul. 21, 2008

(87) PCT Pub. No.: WO2006/069998
PCT Pub. Date: Jul. 6, 2006

(65) Prior Publication Data
US 2009/0208437 A1    Aug. 20, 2009

(30) Foreign Application Priority Data

| Dec. 27, 2004 | (DE) | 10 2004 063 726 |
|---|---|---|
| Dec. 27, 2004 | (DE) | 10 2004 063 728 |
| Jun. 23, 2005 | (DE) | 10 2005 029 385 |
| Jun. 23, 2005 | (DE) | 10 2005 029 386 |
| Jun. 23, 2005 | (DE) | 10 2005 029 387 |
| Jun. 23, 2005 | (DE) | 10 2005 029 388 |
| Jun. 23, 2005 | (DE) | 10 2005 029 389 |
| Jun. 23, 2005 | (DE) | 10 2005 029 390 |

(51) Int. Cl.
*A61K 8/00* (2006.01)
*A61K 8/18* (2006.01)
*A61Q 15/00* (2006.01)

(52) U.S. Cl. ........ 424/65; 424/70.1; 424/78; 424/600; 424/682; 424/684; 514/23; 514/25; 514/54; 514/55; 514/424

(58) Field of Classification Search .......... None
See application file for complete search history.

(56) References Cited

U.S. PATENT DOCUMENTS

| 3,400,197 A | 9/1968 | Lippmann |
|---|---|---|
| 4,526,780 A * | 7/1985 | Marschner et al. ............. 424/66 |
| 4,885,282 A | 12/1989 | Thornfeldt |
| 5,645,854 A | 7/1997 | Masiz |
| 5,770,185 A | 6/1998 | Wachter et al. |
| 5,939,056 A | 8/1999 | Fletcher et al. |
| 5,962,505 A | 10/1999 | Bobrove et al. |
| 6,433,033 B1 | 8/2002 | Isobe et al. |
| 6,475,467 B1 | 11/2002 | Keller et al. |
| 6,645,466 B1 | 11/2003 | Keller et al. |
| 6,723,311 B1 | 4/2004 | Seipel et al. |
| 6,911,210 B1 | 6/2005 | Bormann et al. |
| 6,916,465 B2 | 7/2005 | Panzer et al. |
| 2001/0036450 A1 | 11/2001 | Verite et al. |
| 2003/0064040 A1* | 4/2003 | Lukacsko ................. 424/65 |
| 2003/0118534 A1 | 6/2003 | Bruning et al. |
| 2003/0133891 A1 | 7/2003 | Panzer et al. |
| 2003/0211134 A1 | 11/2003 | Wassenaar |
| 2004/0209954 A1 | 10/2004 | Lukacsko |
| 2004/0253187 A1 | 12/2004 | Kux et al. |
| 2005/0222276 A1 | 10/2005 | Schmaus et al. |

FOREIGN PATENT DOCUMENTS

| DE | 40 09 347 A1 | 9/1991 |
|---|---|---|
| DE | 41 07 153 A1 | 9/1992 |
| DE | 195 16 705 | 11/1996 |
| DE | 198 02 205 A1 | 7/1999 |
| DE | 199 24 496 A1 | 11/2000 |
| DE | 101 58 224 A1 | 5/2002 |
| DE | 101 36 404 A1 | 2/2003 |
| DE | 101 40 586 A1 | 3/2003 |
| DE | 101 47 545 A1 | 4/2003 |
| DE | 101 63 838 A1 * | 7/2003 |
| DE | 102 58 992 A1 | 7/2004 |
| DE | 103 55 712 A1 | 6/2005 |
| EP | 0 319 168 A1 | 6/1989 |
| EP | 0 400 546 A1 | 12/1990 |
| GB | 1080960 | 8/1967 |
| GB | 1113860 | 5/1968 |
| WO | 86/02272 A1 | 4/1986 |

(Continued)

OTHER PUBLICATIONS

English language abstract of 101 58 224 A1.
English language abstract of 40 09 347 A1.
English language abstract of 101 40 586 A1.
English language abstract of 101 36 404 A1.
English language abstract of 199 24 496 A1.
English language abstract of 101 63 838 A1.
English language abstract of 198 02 205 A1.
English language abstract of 102 58 992 A1.
English language abstract of 41 07 153 A1.
English language abstract of 103 55 712 A1.
English language abstract of 101 47 545 A1.

*Primary Examiner* — Carlos Azpuru
*Assistant Examiner* — David Browe
(74) *Attorney, Agent, or Firm* — Abel Law Group, LLP.

(57) ABSTRACT

Glycopyrronium bromide, derivatives and/or isomers thereof in combination with one or more active substances selected from a list of substances as recited in the claims and/or in the form of a W/Si emulsion, an O/W gel, a soap gel stick, and/or a surfactant-containing cleansing formula, and corresponding cosmetic preparations, in particular deodorant/antiperspirant preparations.

24 Claims, 3 Drawing Sheets

FOREIGN PATENT DOCUMENTS

| | | |
|---|---|---|
| WO | 98/00133 A1 | 1/1998 |
| WO | 01/08681 A1 | 2/2001 |
| WO | 03/026585 A2 | 4/2003 |
| WO | 2004/093792 A2 | 11/2004 |

* cited by examiner

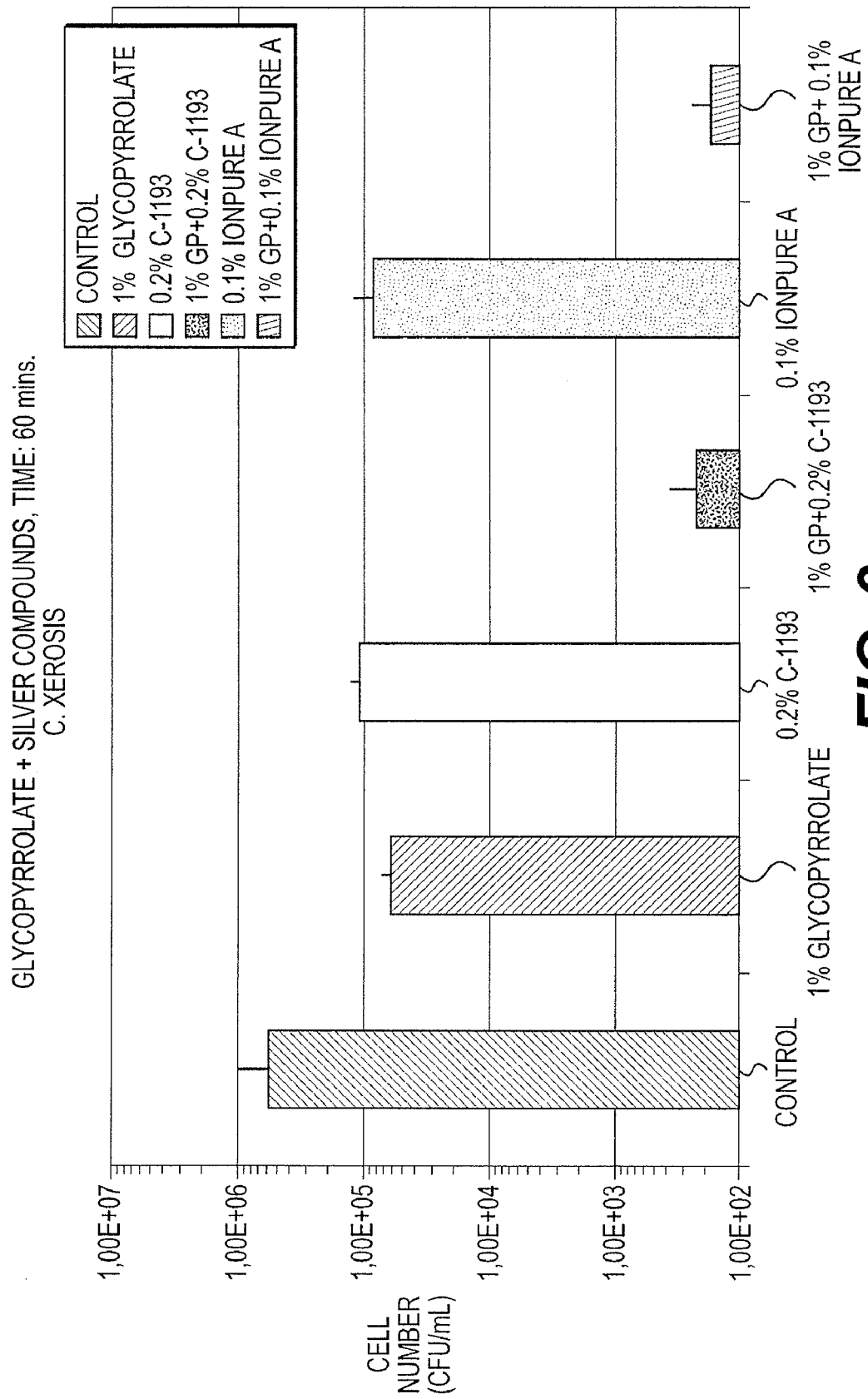

GLYCOPYRROLATE IN COSMETIC PREPARATIONS

BACKGROUND OF THE INVENTION

1. Field of the Invention

The present invention relates generally to the use of glycopyrronium bromide, derivatives and/or isomers thereof in combination with one or more specified active substances and/or in a specified form in cosmetic preparations, in particular deodorant/antiperspirant preparations.

2. Discussion of Background Information

Human beings have two types of sweat glands. The eccrine sweat glands secrete mainly salt and water and do not usually contribute to the development of odors. The apocrine sweat glands are responsible for odor: they secrete fatty acids, cholesterols and other compounds. These substances are decomposed on the skin by bacteria, the break-down products producing the typical odor of sweat.

In order to suppress sweat odor over a longer period, the use of cosmetic preparations is indispensable. The customary cosmetic deodorants are based on different principles, which can also be combined: on the one hand active deodorant ingredients are used, which suppress the growth of the bacteria causing the sweat odor. These germination inhibiting (bacteriostatic) agents include, e.g., triclosan, chlorhexidine or the naturally occurring compounds such as farnesol and phenoxyethanol.

On the other hand, antiperspirants are used, which prevent sweat secretion by blocking the sweat gland outlets. In by far the most antiperspirants, the formation of sweat can be reduced through astringents—primarily aluminum salts such as aluminum hydroxychloride (aluchlorohydrate) or aluminum/zirconium salts.

The combination of astringents with antimicrobially active substances in one and the same composition is also customary. Furthermore, perfumes are used to cover the smell of sweat.

One disadvantage with the use of aluminum chlorohydrate is, e.g., that residues can discolor clothing in an unpleasant manner and the low pH value (acidic) of the cosmetic preparation negatively affects the biological balance of the skin.

In addition to the liquid deodorants, such as atomizers and roll-ons, solid preparations, e.g., deodorant sticks, powder, powder sprays, feminine hygiene agents, etc. are known and common.

The following prerequisites are associated with a satisfactory deodorant/antiperspirant agent, preferably only deodorants, the realization of which prerequisites represents the object of the present invention: 1) protection of the natural biology of the skin, 2) neutral scent, 3) effectiveness only with regard to deodorizing, i.e., only the avoidance and/or elimination of body odor 4) avoidance of the formation of resistant strains of bacteria 5) avoidance of the accumulation of the active agents on the skin 6) harmless in the case of overdosing or other unintended use 7) good cosmetic application 8) ease of use (e.g., as a liquid) and universal application in various cosmetic and external preparations 9) excellent tolerance by the skin and mucous membranes 10) use of environmentally friendly substances.

Glycopyrronium bromide (international nonproprietary name for (±)-(R*)-3-[(S*)-(cyclopentyl hydroxyphenylacetoxy]-1,1-dimethylpyrrolidiniumbromide) is an anticholinergic and spasmolytic known since 1960. It is referred to as "glycopyrrolate" chiefly in English usage, and is characterized by the following chemical structure:

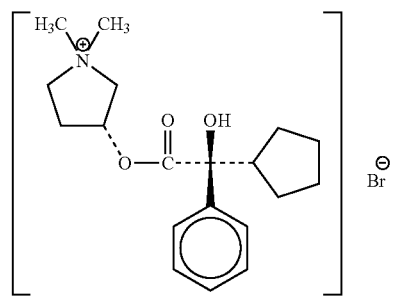

Glycopyrrolate exhibits no or only slight antimicrobial effectiveness.

In the prior art it is based primarily on the use of glycopyrrolate-containing compositions for treating pathological sweating, such as primary or secondary hyperhidrosis, gustatory sweating (Frey's Syndrome).

Anaesthesia, 1983, Volume 38, pages 1195-1204, describes the use of glycopyrrolate in anesthesia. An overview is provided of the pharmacological aspects of glycopyrrolate, the anticholinergic properties and the suitability for reducing sweat gland activity being mentioned.

L. V. Allen, "Topical Agent Stops Facial Sweating," Pharmacist, July 1998, discloses a glycopyrrolate and other pharmaceutical/cosmetic auxiliaries containing formulations for treating gustatory sweating and for treating Frey's Syndrome.

C. L. Hays et al., "The Frey Syndrome: A Simple, Effective Treatment," Otolaryngol Head Neck Surg. 1982, 90, 419-425, describes a clinical comparative study on the topical treatment of gustatory sweating (Frey's Syndrome) with scopolamine and glycopyrrolate. This deals with pathological sweating. Based on the action mechanism of glycopyrrolate, it is disclosed that glycopyrrolate blocks the nerve stimulus of the skin's sweat cells that leads to primary sweat formation, and thereby exhibits fewer side effects than scopolamine, since as a quarternary ammonium compound it does not pass through the blood-brain barrier and penetrates biological membranes more slowly.

WO03/026585 describes the use of glycopyrronium bromide to inhibit eccrine perspiration in humans—although the effect of glycopyrronium bromide and its use against hyperhidrosis has been known for much longer.

WO-A-01/08681 discloses the treatment of a number of pathological conditions with compositions based on glycopyrrolate, a special anticholinergic amine. The conditions include gustatory sweating and "Frey's Syndrome," which is understood to mean increased sweat formation in the auriculotemporal area, which can be triggered by local irritation and by certain foods. In addition hyperhidrosis (increased sweat secretion) is mentioned. Formulations are disclosed, which are suitable for topical application to the skin, such as ointments, creams, gels and pastes, and which a pharmaceutically tolerated carrier.

U.S. Pat. No. 6,433,033 discloses compositions containing 0.25 to 6% by weight, in particular 0.5 to 4% by weight glycopyrrolate together with other pharmaceutically acceptable constituents. This composition is used to treat hyperhidrosis and is applied topically.

WO-A-03/011340 discloses a pharmaceutical formulation containing glycopyrrolate or salts or derivatives thereof, in a quantity between 0.05 and 20% by weight and also a vehicle such as a gel and/or colloidal carrier system. The glycopyrrolate formulations are applied topically to treat hyperhidrosis.

SUMMARY OF THE INVENTION

The object of the present invention is to provide a cosmetic preparation that

- Shows an improved antiperspirant effect,
- Shows an improved deodorizing effect,
- Exhibits a skin-care property and is characterized by improved skin-care action,
- Helps to avoid a stickiness of the preparation that is undesirable in sensory terms,
- Helps to avoid an undesirable clouding of the preparation,
- Causes less strain on the biological balance of the skin through skin neutrality,
- Serves better as a vehicle for cosmetic and medicinal/dermatological active agents,
- Is characterized by improved physicochemical stability of the formula,
- Is characterized by improved biocompatibility and/or
- Improved sensory properties, such as, e.g., ease of dispersion on or absorption into the skin than the active agents, active agent combinations and preparations of the prior art.

This combination of objects is attained by a cosmetic preparation according to the main claims. Advantageous embodiments of the preparations according to the invention and their use are the subject of the dependent claims.

It was surprising and not foreseeable to one skilled in the art that the objects are attained by a combination of active agents and a cosmetic preparation comprising same, comprising glycopyrronium bromide, derivatives thereof and/or isomers in combination with one or more active substances selected from the group a.) polyethylene glycol (2) stearyl ether and polyethylene glycol (21) stearyl ether,
b.) surface-active substances A, selected from the group of glucose derivatives, which are characterized by the formula

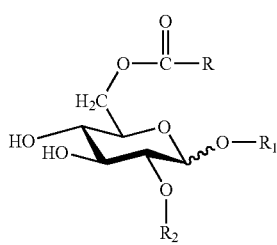

R being a branched or unbranched alkyl radical having 1 to 24 carbon atoms, R1 being either a hydrogen atom or a branched or unbranched alkyl radical having 1 to 24 carbon atoms and R2 being a hydrogen atom or a branched or unbranched acyl radical having 1 to 24 carbon atoms,
whereby one or more surface-active substances B can also be contained, selected from the group of substances with the general structural formula

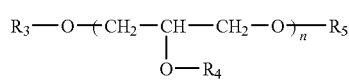

R3, R4 and R5 being selected independently of one another from the group that comprises: H, branched or unbranched, saturated or unsaturated fatty acid radicals having 8 to 24 carbon atoms, wherein up to three aliphatic hydrogen atoms can be substituted by hydroxy groups and n is a number between 2 and 8,
c.) one or more partially neutralized esters of monoglycerides and/or diglycerides of saturated fatty acids with citric acid,
d.) one or more polyols from the group comprising ethylene glycol, glycerin, octoxyglycerin (2-ethylhexyl glycerin ether) and $C_4$-$C_{12}$ alkane diols, preferably 1,2 decane diol
e.) one or more dialkyl-substituted acetic acids,
f.) one or more hydrocolloids, selected from the group of the organically natural or modified natural, organically synthetic or inorganically water-soluble polymers,
g.) one or more mono-, oligo- and/or polysaccharides,
h.) the silicates in combination with oils,
i.) the oils, which are selected from the group of alkylbenzoates, ester oils, dialkyl carbonates and ethers, linear and/or branched-chain, aliphatic hydrocarbons and/or short-chain hydrocarbon esters, in particular isopropyl esters,
j.) perfumes, selected from the group of aldehydes, esters, ionones, methylionone, damascones, salicylates, acetals and/or wood bodies, in particular Iso E Super,
k.) phenoxy ethanol and/or
l.) antimicrobially active agentiferous glasses and/or in the form of
m.) a W/Si emulsion,
n.) an O/W gel or
o.) a soap gel stick.

BRIEF DESCRIPTION OF THE DRAWINGS

In the accompanying drawings,

FIG. 3 is a graph representing the reduction of cell numbers (*C. xerosis*) obtained with preparations which contain glycopyrrolate and agentiferous glass, both individually and in combination.

DETAILED DESCRIPTION OF THE INVENTION

Figure 1:
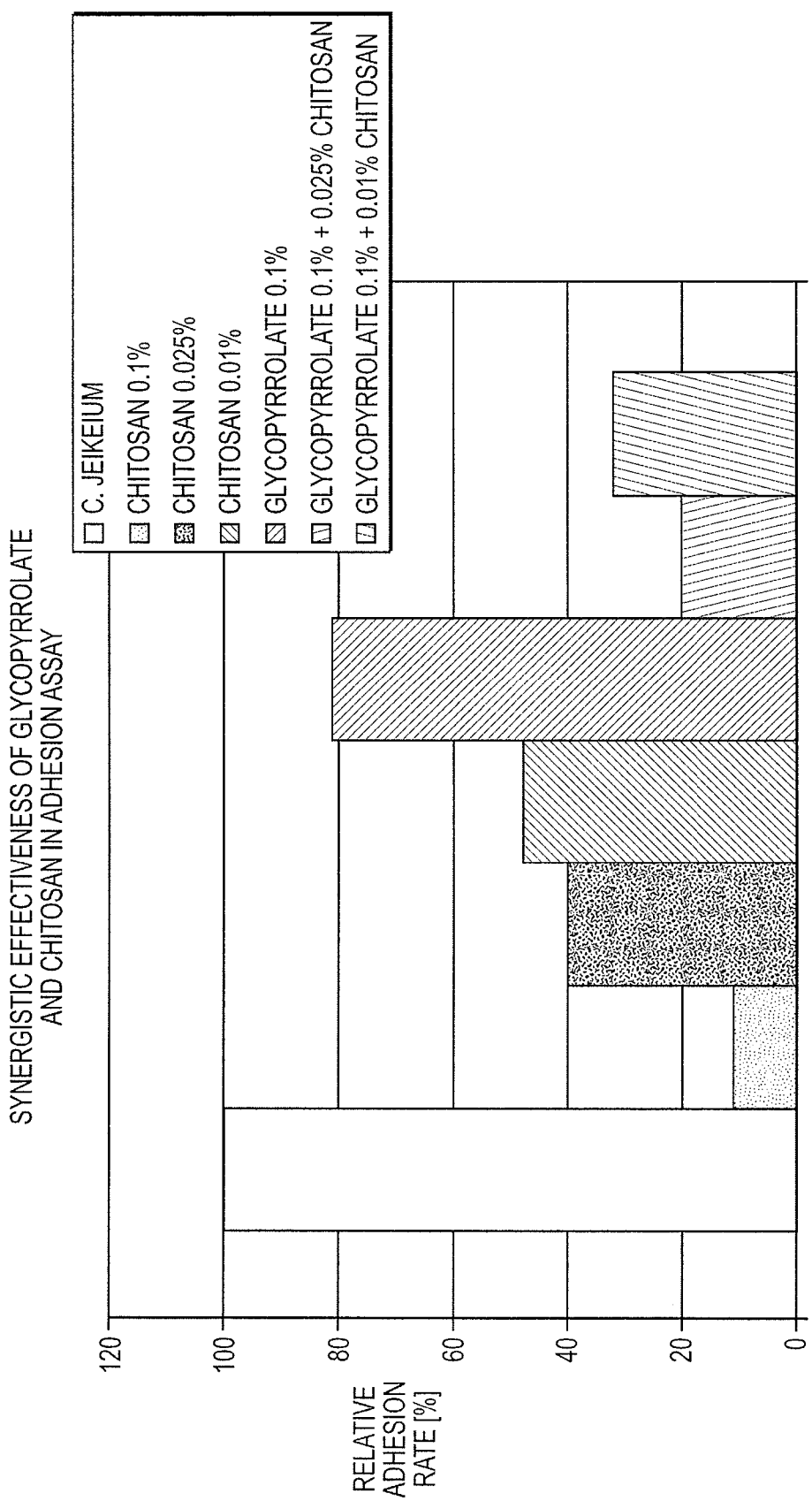
FIG. 1 is a graph representing the relative effectiveness of glycopyrrolate and chitosan, both individually and in combination, in an adhesion assay.

According to the invention, glycopyrrolate or glycopyrronium bromide (international nonproprietary name for (±)-(R*)-3-(cyclopentyl hydroxyphenylacetoxy]-1,1-dimethylpyrrolidiniumbromide), is used synonymously below for derivatives thereof and isomers. Glycopyrronium bromide, characterized by the following chemical structure:

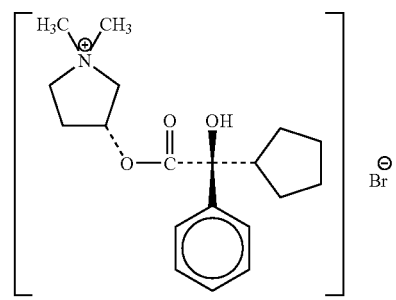

is preferred.

Glycopyrrolate has no or only slight antimicrobial effectiveness. However, in combination with the active substances or forms a) through o) determined according to the invention, it is surprisingly shown that the antimicrobial effectiveness and thus also the antiperspirant effectiveness and in particular the deodorizing effectiveness is increased above average.

Glycopyrrolate thus also serves as an enhancer for antimicrobial agents. Surprisingly and not to be expected by one skilled in the art, it was possible to show that glycopyrrolate alone in the formulations used does not show any antibacterial effect, but in combination with other active agents, such as in particular antimicrobially active aluminum salts or silver salts, leads to a significantly better antimicrobial effect than the active agents alone without glycopyrrolate.

The addition of deodorizing/antiperspirant agents, such as antimicrobially active aluminum salts, such as, e.g., aluminum chlorohydrate (ACH), is thus preferred but not absolutely necessary.

This effect is based on the fact that glycopyrrolate incorporates itself in the membrane of the bacteria similar to a surfactant. Although this incorporation alone is not sufficient to destroy the bacteria, this makes them more susceptible to attack by antibacterial substances (deodorizing/antiperspirant agents) which can pass through or even destroy the membrane due to the impaired membrane integrity.

It has been shown that GLYCOPYRROLATE in combination with polyethylene glycol (2) stearyl ether and polyethylene glycol (21) stearyl ether shows very positive effects.

Polyethylene glycol (2) stearyl ether is a known W/O emulsifier.

Polyethylene glycol (21) stearyl ether is a known O/W emulsifier. Both cited emulsifiers are often used together as an emulsifier system or as part of an emulsifier system.

Following thorough tests it was surprising and not foreseeable that the combinations of glycopyrronium bromide, polyethylene glycol (2) stearyl ether and polyethylene glycol (21) stearyl ether, emulsions containing active agent combinations of glycopyrronium bromide, polyethylene glycol (2) stearyl ether and polyethylene glycol (21) stearyl ether, and the use of active agent combinations of this type as an active principle of cosmetic deodorants and antiperspirants, eliminate the disadvantages of the prior art and above all help to completely attain the objects.

The addition of polyethylene glycol (2) stearyl ether and polyethylene glycol (21) stearyl ether increases the antiperspirant effect of glycopyrronium bromide in a surprising and not foreseeable manner.

It has proven to be particularly advantageous if the active agent combinations or preparations are characterized in that the following weight ratios are established:
(A:B:C) is selected as a:b:c, a, b and c independently of one another being positive rational numbers from 1 to 200, preferably from 1 to 50.
A represents the concentration of glycopyrronium bromide in weight units (e.g., % by weight),
B represents the concentration of polyethylene glycol (2) stearyl ether in the same weight units,
C represents the concentration of polyethylene glycol (21) stearyl ether in the same weight units,
in each case based on the total weight of the preparation.

Furthermore, it has proven to be advantageous to select the ratios (B+C)/A, A, B and C having the properties described above, from the range between 0.5 and 200, preferably from the range between 1 and 50.

The active agent combinations according to the invention are preferably present in O/W emulsions.

A particularly advantageous deodorant/antiperspirant effect is achieved in the combination of GLYCOPYRROLATE and the specific surface-active substances. The combination of glycopyrronium bromide and one or more surface-active substances A, selected from the group of glucose derivatives, which are characterized by the structural formula

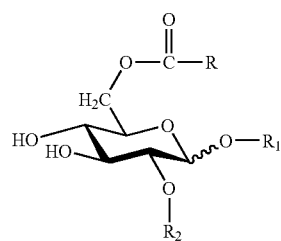

R being a branched or unbranched alkyl radical having 1 to 24 carbon atoms, R1 being either a hydrogen atom or a branched or unbranched alkyl radical having 1 to 24 carbon atoms, and R2 being either a hydrogen atom or a branched or unbranched acyl group having 1 to 24 carbon atoms, in addition one or more surface-active substances B, selected from the group of substances with the general structural formula

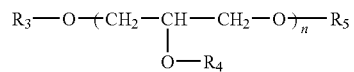

R3, R4 and R5 independently of one another being selected from the group comprising H, branched or unbranched, saturated or unsaturated fatty acid radicals having 8 to 24 carbon atoms, wherein up to three aliphatic hydrogen atoms can be substituted by hydroxy groups and n is a number between 2 and 8, eliminates in cosmetic preparations the disadvantages of the prior art.

The addition of surface-active glucose derivatives and oligoglycerin ether derivatives increases the antiperspirant action of glycopyrronium bromide in a surprising and not foreseeable manner.

The surface-active glucose derivatives A are particularly advantageously selected from the group methylglucose monostearate (formula as follows)

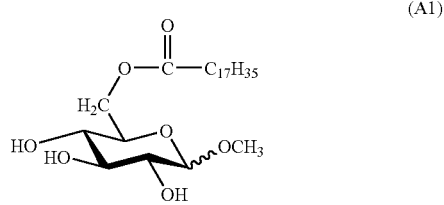

or methylglucose distearate (formula as follows)

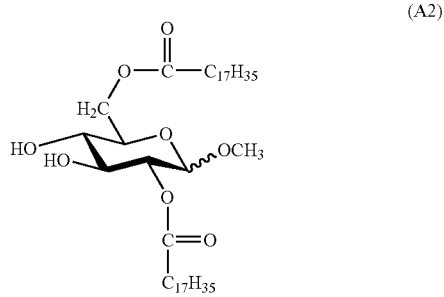

and any desired mixtures thereof, e.g., approximately equimolar mixtures thereof, which are also called methylglucose sesquistearate. Such methylglucose sesquistearate is available commercially, for example under the trade name Tego® Care PS from Th. Goldschmidt KG.

Particularly advantageously the surface-active substances B are chosen from the group of compounds in which n assumes the value 3, and R3, R4 and R5, independently of one another, are chosen from the group which consists of: H, branched or unbranched, saturated or unsaturated fatty acid radicals having from 14 to 20 carbon atoms, in particular the triglyceryl dicarboxylates with the general structure listed below:

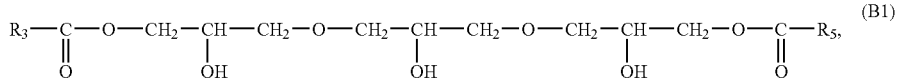

As an emulsifier combination that is preferred according to the invention, it has proven preferable to use an approximately equimolar mixture of compounds A2 and B1, where, in B1, the radicals R3 and R5 are preferably both a stearate radical. Such emulsifier combinations are available as "polyglyceryl(3) methylglucose distearate (PGMS), under the trade name Tego Care® 450 from Th. Goldschmidt KG.

In accordance with the use according to the invention, the deodorants are particularly advantageously characterized in that the surface-active substances A, selected from the group of glucose derivatives, are present in concentrations from 0.01-10.00% by weight, preferably 0.05-5.00% by weight, particularly preferably 0.1-3.00% by weight, in each case based on the total weight of the preparation.

In accordance with the use according to the invention, the deodorants are particularly advantageously characterized in that the surface-active substances B are present in concentrations of 0.01-10.00% by weight, preferably 0.05-5.00% by weight, particularly preferably 0.1-3.00% by weight, in each case based on the total weight of the preparation.

An active agent combination of glycopyrronium bromide and one or more partially neutralized esters of monoglycerides and/or diglycerides of saturated fatty acids with citric acid or cosmetic preparations containing such active agent combinations, and the use of such active agent combinations as the active principle of cosmetic deodorants and antiperspirants, eliminates the disadvantages of the prior art in the manner according to the invention.

One particularly advantageous citric ester is glyceryl stearate citrate. Such citric esters are obtainable, for example, under the product name "IMWITOR®370" from SASOL.

It is advantageous according to the invention to select the molar ratio of glycopyrronium bromide to one or more partially neutralized esters of monoglycerides and/or diglycerides of saturated fatty acids with citric acid from the range of 100:1 to 1:100, preferably 50:1 to 1:50, in particularly preferably 20:1 to 1:20.

Surprisingly, the objects described are also attained through an active agent combination or cosmetic preparations containing it, comprising glycopyrronium bromide and one or more polyols from the group comprising ethylene glycol, glycerin, octoxyglycerin (2-ethylhexylglycerin ether) and the $C_4$-$C_{12}$-alkane diols, preferably 1,2-decanediol.

The use of active agent combinations of this type as an active principle of cosmetic deodorants and antiperspirants eliminates the disadvantages of the prior art.

The preparations according to the invention are characterized by a high degree of effectiveness with at the same time a very good skin tolerance. Moreover, they have excellent sensory properties and only a slight feeling of stickiness on the skin.

$C_4$-$C_{12}$-Alkane diols which are preferred according to the invention are the corresponding 1,2-diols with unbranched alkyl chains, 1,2-decanediol is particularly preferred.

Figure 2:
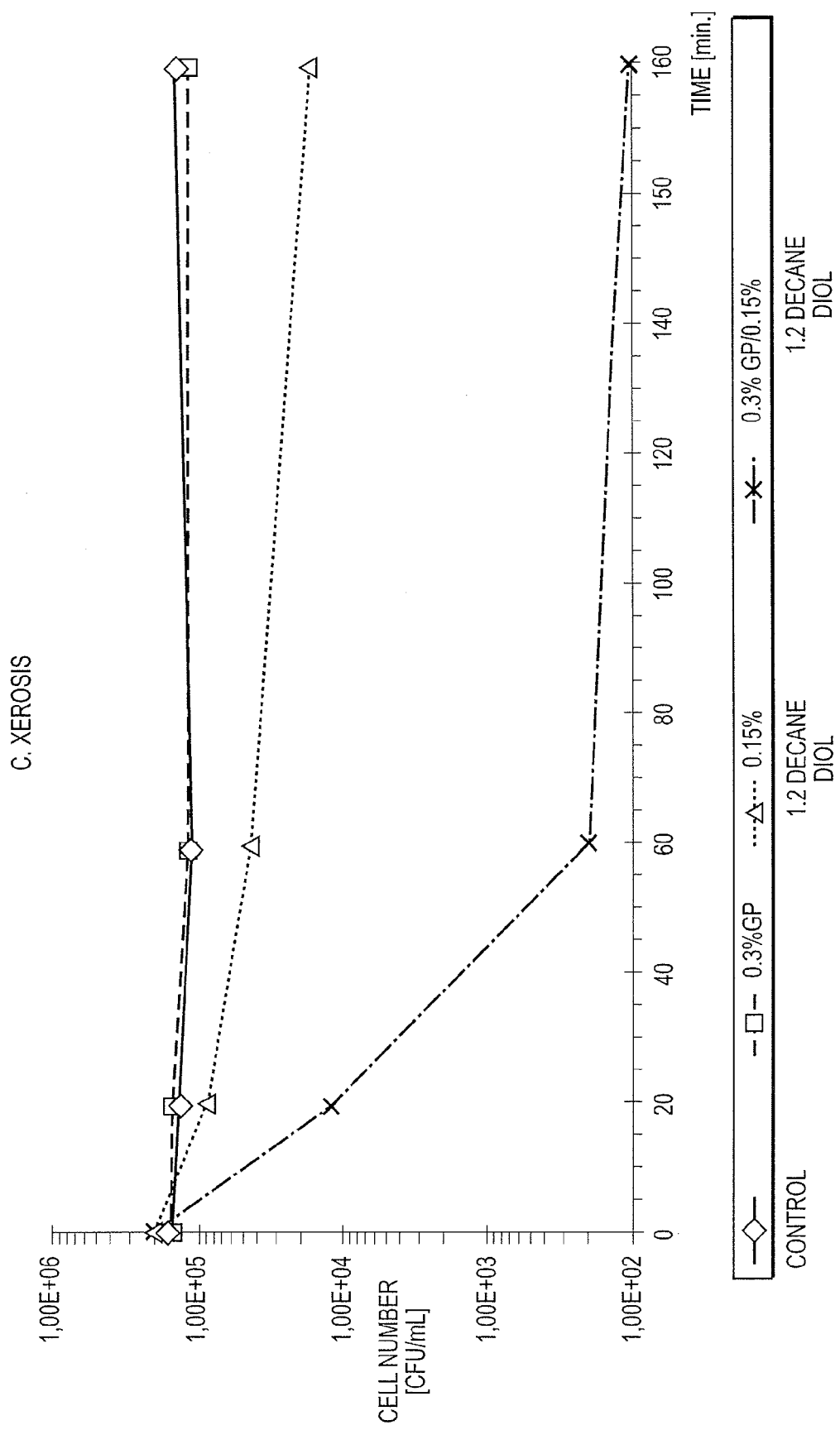
FIG. 2 is a graph representing the reduction of cell numbers (*C. xerosis*) obtained with preparations which contain glycopyrrolate and 1,2-decandiol, both individually and in combination.

As shown in FIG. 2, the combination of 0.3% by weight of GLYCOPYRROLATE and 0.15% by weight of 1,2-decane diol shows a synergistic increase in the reduction of the cell numbers (C. xerosis) compared to the preparations containing respectively only GLYCOPYRROLATE or 1,2-decanediol.

This in turn impressively substantiates the synergistic effect of the combination of GLYCOPYRROLATE with the active agents according to the invention with regard to the deodorizing and antiperspirant effect.

However, advantageous embodiments of the present invention are also 2-methyl propanediol, 1,5-pentanediol, 2,4-pentanediol, 1,6-hexanediol, 2,5-hexanediol, 1,8-octanediol, 1,10-decanediol, 1,12-dodecanediol.

It is advantageous according to the invention to select the molar ratio of glycopyrronium bromide to polyol from the range of 100:1 to 1:100, preferably 50:1 to 1:50, in particular preferably 20:1 to 1:20.

According to the use according to the invention, the deodorants are particularly advantageously characterized in that the polyols are present in concentrations of 0.01-20.00% by weight, preferably 0.1-10.00% by weight, in each case based on the total weight of the preparation.

The objects are also partially or completely attained through the combination of GLYCOPYRROLATE with dialkyl acetic acids.

It is known that certain dialkyl-substituted acetic acids are used as preservatives due to their bactericidal effect on a number of microorganisms. The use of dialkyl-substituted acetic acids as antibacterial, antifungal or antiviral active agents is thus known from DE-OS 19516705.

However, it was still surprising and not foreseeable after all this that active agent combinations of glycopyrronium bromide and one or more dialkyl-substituted acetic acids or cosmetic preparations containing such active agent combinations, and the use of such active agent combinations as the active principle of cosmetic deodorants and antiperspirants, eliminate the disadvantages of the prior art.

According to the invention it is therefore possible to obtain deodorizing and/or antiperspirant preparations with better performance than the individual substances would have indicated.

Dialkyl-substituted acetic acids with the formula

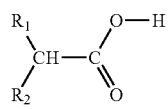

are advantageous for the purposes of the present invention, $R_1$ being a branched or unbranched alkyl radical having 1-12 carbon atoms and $R_2$ being a branched or unbranched alkyl radical having 1-24 carbon atoms.

The alkyl radicals are advantageously selected such that $R_1$=methyl, ethyl, propyl, butyl, pentyl or hexyl.

Furthermore, the alkyl radicals are advantageously selected such that $R_2$=octyl, nonyl, decyl, undecyl, dodecyl.

It is advantageous in particular to select the acetic acid derivatives from the group of 2-butyl octanoic acid, 2-butyl decanoic acid, 2-hexyl octanoic acid, 2-hexyl decanoic acid.

2-Butyl octanoic acid is very particularly preferred.

It is advantageous according to the invention to select the molar ratio of glycopyrronium bromide to dialkyl-substituted acetic acids from the range of 100:1 to 1:100, preferably 50:1 to 1:50, particularly preferably 20:1 to 1:20.

The active agent combinations or cosmetic preparations containing them, comprising glycopyrronium bromide and at least one or more hydrocolloids, e.g., as a polymeric thickener, selected from the group of—organically natural or modified natural, —organically synthetic or—inorganically, water-soluble polymers, eliminate the disadvantages of the prior art.

"Hydrocolloid" is the technical abbreviation for the actually more correct term "hydrophilic colloid." Hydrocolloids are macromolecules that have a largely linear form and have intermolecular interaction forces that render possible secondary valence bonds and primary valence bonds between the individual molecules and thus the formation of a reticular structure. They are in part water-soluble natural or synthetic polymers that form gels or viscous solutions in aqueous systems. They increase the viscosity of the water by either binding water molecules (hydration) or absorbing and encasing the water in their macromolecules intertwined with one another, at the same restricting the mobility of the water. Such water-soluble polymers represent a large group of chemically very different natural and synthetic polymers, the common feature of which is their solubility in water or aqueous media. The prerequisite for this is that these polymers have a sufficient number of hydrophilic groups for the water solubility and are not too highly crosslinked. The hydrophilic groups can be of a non-ionic, anionic or cationic nature, e.g., as follows:

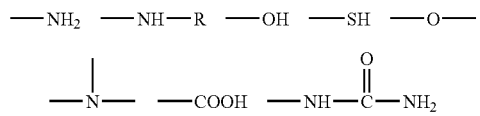

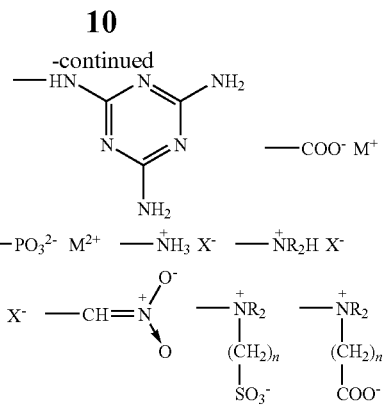

The group of cosmetically and dermatologically relevant hydrocolloids can be divided as follows:

organic, natural compounds, such as, for example, agar agar, carrageen, tragacanth, gum arabic, alginates, pectins, polyoses, guar flour, carob bean flour, starch, dextrins, gelatin, casein, organic, modified natural substances, such as, for example, carboxymethylcellulose and other cellulose ethers, hydroxyethyl- and -propyl-cellulose and microcrystalline cellulose and the like, organic, fully synthetic compounds, such as, for example, polyacrylic and polymethacrylic compounds, vinyl polymers, polycarboxylic acids, polyethers, polyimines, polyamides, polyurethanes, inorganic compounds, such as, for example, polysilicic acids, clay minerals, such as montmorillonite, zeolites, silicas.

Microcrystalline cellulose is an advantageous hydrocolloid for the purposes of the present invention. It is available, e.g., from "FMC Corporation Food and Pharmaceutical Products" under the trade name Avicel®. A particularly advantageous product for the purposes of the present invention is the type Avicel® RC-591, which is a modified microcrystalline cellulose, which is composed of 89% microcrystalline cellulose and 11% sodium carboxymethyl cellulose. Further commercial products of this raw material class are Avicel® RC/CL, Avicel® CE-15 and Avicel® 500.

Further hydrocolloids which are advantageous according to the invention are, for example, methylcelluloses, which is the name for the methyl ethers of cellulose. They are characterized by the following structural formula

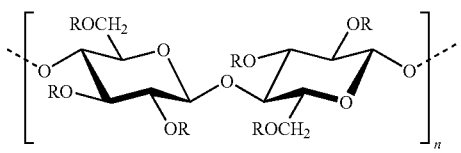

in which R can be a hydrogen or a methyl group.

Particularly advantageous for the purposes of the present invention are the cellulose mixed ethers, which are generally likewise referred to as methylcelluloses, which contain, in addition to a dominating content of methyl groups, additionally 2-hydroxyethyl, 2-hydroxypropyl and 2-hydroxybutyl groups. Particular preference is given to (hydroxypropyl)methylcelluloses, for example those available under the trade name Methocel® E4M from Dow Chemical Comp.

Also advantageous according to the invention is sodium carboxymethylcellulose, the sodium salt of the glycolic ether of cellulose, for which R in structural formula I can be a hydrogen and/or $CH_2$—COONa. Particular preference is given to hydrophobically modified hydroxyethylcelluloses, as available under the trade name Natrosol® Plus 330 CS from Aqualon. Other cellulose derivatives according to the invention are the ethylhydroxyethylcellulose (Elfacos CD 481 from Akzo Nobel).

For the purposes of the present invention, preference is also given to xanthan (CAS No. 11138-66-2), also called xanthan gum, which is an anionic heteropolysaccharide which is generally formed by fermentation from maize sugar and is isolated as the potassium salt. It is produced by *Xanthomonas campestris* and a few other species under aerobic conditions with a molecular weight of $2 \times 10^6$ to $24 \times 10^6$. Xanthan is formed from a chain having β-1,4-bonded glucose (cellulose) with side chains. The structure of the subgroups consists of glucose, mannose, glucuronic acid, acetate and pyruvate. The number of pyruvate units determines the viscosity of the xanthan.

For the purposes of the present invention, another advantageous gel former is carrageen, a gel-forming extract with a similar structure to agar, of North Atlantic red algae which belong to the Florideae (*Chondrus crispus* and *Gigartina stellata*).

The term carrageen is frequently used for the dried algae product and carrageenan for the extract thereof. The carrageen precipitated from the hot-water extract of the algae is a colorless to sand-colored powder with a molecular weight range from 100,000-800,000 and a sulfate content of about 25%. Carrageen is very readily soluble in warm water and forms a thixotropic gel on cooling, even if the water content is 95-98%. The rigidity of the gel is effected by the double helix structure of the carrageen. In the case of carrageenan, three principal constituents are differentiated: the gel-forming κ fraction consists of D-galactose 4-sulfate and 3,6-anhydro-α-D-galactose, having alternate glycoside bonds in the 1,3- and 1,4-positions (agar, in contrast, contains 3,6-anhydro-α-L-galactose). The non-gelling λ fraction is composed of 1,3-glycosidically linked D-galactose 2-sulfate and 1,4-bonded D-galactose 2,6-disulfate radicals and is readily soluble in cold water. ι-Carrageenan, composed of D-galactose 4-sulfate in 1,3-bond and 3,6-anhydro-α-D-galactose 2-sulfate in 1,4-bond, is both water-soluble and also gel-forming. Other types of carrageen are likewise labeled with Greek letters: α, β, γ, μ, ν, ξ, π, ω, χ. The nature of cations which are present ($K^+$, $NH_4^+$, $Na^+$, $Mg^{2+}$, $Ca^{2+}$) also influences the solubility of the carrageens.

The use of chitosan in cosmetic preparations is known per se. Chitosan represents a partially deacylated chitin. This biopolymer has, inter alia, film-forming properties and is characterized by a silky feel on the skin. A disadvantage, however, is its severe stickiness on the skin which occurs in particular—temporarily—during application. In individual cases corresponding preparations may not then be marketable since they are unacceptable to and viewed negatively by the consumer. As is known, chitosan is used, for example, in hair care. It is suitable, to a better degree than the chitin on which it is based, as a thickener or stabilizer and improves the adhesion and water resistance of polymeric films. A representative of the large number of literature references for the prior art is: H. P. Fiedler, "Lexikon der Hilfsstoffe fur Pharmazie, Kosmetik und angrenzende Gebiete", third edition 1989, Editio Cantor, Aulendorf, p. 293, keyword "Chitosan."

Chitosan is characterized by the following structural formula:

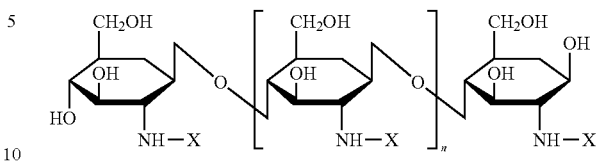

where n assumes values up to about 10,000, and X is either the acetyl radical or hydrogen. Chitosan forms by a deacetylation and partial depolymerization (hydrolysis) of chitin, which is characterized by the structural formula

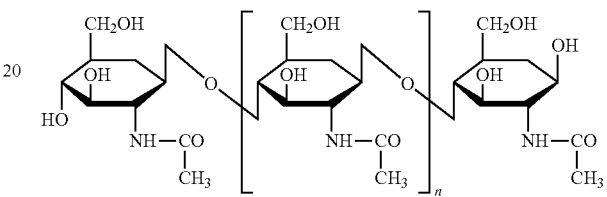

Chitin is an essential constituent of the ecto skeleton [ωχιτων=Greek: integument] of arthropods (e.g., insects, crabs, spiders) and is also found in supporting tissues of other organisms (e.g., molluscs, algae, fungi).

In the region of about pH<6, chitosan is positively charged and in that range is also soluble in aqueous systems. It is incompatible with anionic raw materials. For this reason, to prepare chitosan-containing oil-in-water emulsions, the use of nonionic emulsifiers suggests itself. These are known per se, for example from EP-A 776 657.

Preference is given according to the invention to chitosans with a degree of deacetylation of >25%, in particular >55-99% [determined by means of $^1$H-NMR]).

Chitosans or chitosan derivatives are particularly preferred with

A. a degree of deacetylation of 75%-98%, in particular 75-85%, 82-85% or 82-84%, as well as 80-98%, preferably 92-98%.

B. a viscosity to 10 mPas, in particular 4-10 mPas, preferably 5-8 mPas,

C. a weight average molecular weight distribution of less than 300,000 Da, preferably less than 160,000 Da or less than 150,000 Da, in particular preferably less than 100,000 Da, and preferably between 20,000-300,000 Da, in particular 50,000-160,000 Da, in particular 50,000-120,000 Da and D. a number average molecular weight distribution of less than 40,000 Da, preferably less than 35,000 Da, in particular less than 27,000 Da, particularly preferably 10,000-35,000 Da, in particular 10,000-27,000 Da.

It is also advantageous to select chitosans with molecular weights between 10,000 and 1,000,000, in particular those with molecular weights between 100,000 and 1,000,000 (determined by means of gel permeation chromatography).

The parameters of the chitosan that are important according to the invention are determined as follows.

The viscosity of a 1% solution is measured according to Brookfield in 1% acetic acid at 25° C.

The molecular weight is determined according to the GLYCOPYRROLATC analysis in a 0.1 molar NaCl/0.1 vol % trifluoroacetic acid solution at 23° C. with a column PSS novema (10 μm, linear, ID 8.0 mm×300 mm), a flow of 1.0 ml/min, a sample concentration of 2.0 g/l and an injection volume of 20 μl.

The deacetylation degree can be measured using the direct titration method.

The chitosans working particularly efficiently have a molecular weight between to 300,000 Da, in particular between 50,000-160,000 Da, a degree of deacetylation of 75-98%, a viscosity of no more than 10 mPas, a number average molecular weight distribution of less than 40,000 Da and are composed of at least 50 monomers.

Chitosans are considered particularly preferable with a molecular weight of less than 160,000 Da, a degree of deacetylation of 78-86%, a viscosity of no more than 10 mPas and a number average molecular weight distribution of less than 35,000 Da.

Chitosans with a molecular weight of less than 100,000 Da, a deacetylation degree of 78-84%, a viscosity of no more than 10 mPas and a number average molecular weight distribution of less than 27,000 Da were shown to be advantageous in particular.

According to the invention, for the special use chitosans according to the invention with the following combinations of the preferred parameter ranges A, B, C and D can be individually chosen, produced and used.

TABLE

Chitosan parameter ranges

| A<br>Degree<br>of<br>Deacetylation [%] | B<br>Viscosity<br>[mPas] | C<br>Weight Average<br>Molecular Weight<br>Distribution<br>[Da] | D<br>Number Average<br>Molecular Weight<br>Distribution<br>[Da] |
|---|---|---|---|
| 75-98 | Max. 10 | <300,000 | <40,000 |
| 78-86 | 4-10 | <160,000 | <35,000 |
| 75-85 | 5-8 | <150,000 | <27,000 |
| 80-98 | | <100,000 | 10,000-35,000 |
| 80-85 | | 20,000-300,000 | 10,000-27,000 |
| 82-84 | | 50,000-160,000 | |
| 92-98 | | 50,000-120,000 | |

Thus for example a preparation containing GLYCOPYRROLATE and chitosans with A=80-98%, B=5-10 mPas, C=50,000-120,000 Da and D=10,000-27,000 Da is as preferred for a special deodorant/antiperspirant product formulation as a preparation containing chitosans with A=82-84%, B=5-8 mPas, C<160,000 Da and D<35,000 Da.

It was surprisingly found that the combination of glycopyrrolate and chitosan and preparations containing this combination reduce the adhesion, i.e., the ability of the microorganisms to adhere to surfaces, so that their usual number on such surfaces is reduced, or also that no or no significant amounts of microorganisms can be detected.

In an adhesion assay with the microorganisms *Corynebacterium jeikeium* (*C. jeikeium*) the synergistic reduction of the adhesion was impressively confirmed, as shown in FIG. 1.

A combination of 0.1% by weight of glycopyrrolate and 0.025 or 0.01% by weight of chitosan reduces the adhesion of the bacterium *C. jeikeium* by more than 50% compared to the use of chitosan of the same proportion without the addition of glycopyrrolate.

The use of glycopyrrolate in combination with chitosan, in particular in proportions of 0.1% by weight of glycopyrrolate and 0.01 to 0.025% by weight of chitosan is thus predestinated.

Polyacrylates are gelling agents which are likewise to be used advantageously for the purposes of the present invention. Polyacrylates which are advantageous according to the invention are acrylate-alkyl acrylate copolymers, in particular those chosen from the group of so-called carbomers or carbopols (Carbopol® is actually a registered trademark of B. F. Goodrich Company). In particular, the acrylate-alkyl acrylate copolymers advantageous according to the invention are characterized by the following structure:

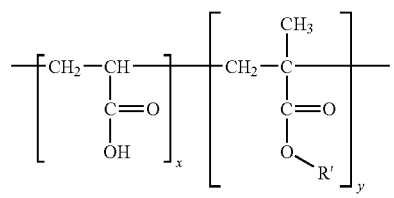

Here R' is a long-chain alkyl radical, and x and y represent numbers which symbolize the respective stoichiometric proportion of each of the comonomers.

According to the invention, particular preference is given to acrylate copolymers and/or acrylate-alkyl acrylate copolymers which are available under the trade names Carbopol® 1382, Carbopol® 981 and Carbopol® 5984 from B. F. Goodrich Company, preferably polyacrylates from the group of carbopols of the types 980, 981, 1382, 2984, 5984 and particularly preferably Carbomer 2001.

Also advantageous are copolymers of $C_{10-30}$-alkyl acrylates and one or more monomers of acrylic acid, of methacrylic acid or esters thereof which are crosslinked with an allyl ether of sucrose or an allyl ether of pentaerythritol.

Compounds which carry the INCI name "Acrylates/$C_{10-30}$ Alkyl Acrylate Crosspolymer" are advantageous. Particularly advantageous are those available under the trade names Pemulen® TR1 and Pemulen® TR2 from B. F. Goodrich Company.

Compounds which bear the INCI name Ammonium Acryloyldimethyltaurate/Vinylpyrrolidone copolymers are advantageous.

According to the invention, the Ammonium Acryloyldimethyltaurate/Vinylpyrrolidone copolymers advantageously have the empirical formula $[C_7H_{16}N_2SO_4]_n [C_6H_9NO]_m$, corresponding to a statistical structure as follows

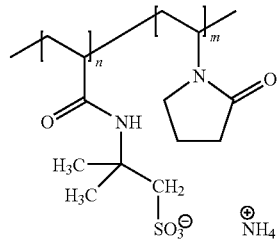

Preferred species for the purposes of the present invention are listed in Chemical Abstracts under the Registry numbers 58374-69-9, 13162-05-5 and 88-12-0 and are available under the trade name Aristoflex® AVC from Clariant GmbH.

Also advantageous are copolymers/crosspolymers comprising Acryloyldimethyl Taurate, such as, for example, Simugel® EG or Simugel® EG from Seppic S. A.

Other hydrocolloids to be used advantageously according to the invention are also water-soluble or dispersible anionic polyurethanes, which can be advantageously obtained from i) at least one compound containing two or more active hydrogen atoms per molecule,
ii) at least one acid or salt group containing diol and
iii) at least one diisocyanate.

The component i) is in particular diols, aminoalcohols, diamines, polyesterols and polyetherols with a number average molecular weight of respectively up to 3000 or mixtures thereof, whereby up to 3 mol % of the specified compounds can be replaced by triols or triamines. In particular the component (i) comprises at least 50% by weight of a polyesterdiol, based on the total weight of the component (i). As polyesterdiols all those can be considered that are customarily used for the production of polyurethanes, in particular conversion products of phthalic acid and diethylene glycol, isophthalic acid and 1,4-butanediol, isophthalic acid/adipic acid and ethylene glycol or 5-$NaSO_3$-isophthalic acid, phthalic acid, adipic acid and 1,6-hexanediol.

Suitable diols are, for example, ethylene glycol, propylene glycol, butylene glycol, neopentyl glycol, polyetherols, such as polyethylene glycols with molecular weights of up to 3000, block copolymers of ethylene oxide and propylene oxide with number average molecular weights of up to 3000 or block copolymers of ethylene oxide, propylene oxide and butylene oxide which contain the copolymerized alkylene oxide units in random distribution or in the form of blocks. Preference is given to ethylene glycol, neopentyl glycol, di-, tri-, tetra-, penta- or hexaethylene glycol. Suitable diols are also poly(hydroxycarboxylic acid) diols.

Suitable aminoalcohols are, for example, 2-aminoethanol, 2-(N-methylamino)ethanol, 3-aminopropanol or 4-aminobutanol.

Suitable diamines are, for example, ethylenediamine, propylenediamine, 1,4-diaminobutane and 1,6-diaminohexane, and also α,ω-diamines which can be prepared by amination of polyalkylene oxides with ammonia.

Component ii) is, in particular, dimethylolpropanoic acid or compounds of the formulae

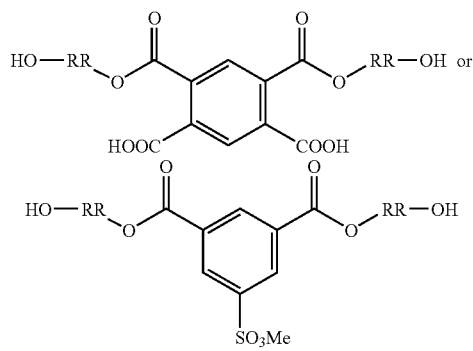

where RR is in each case a $C_2$-$C_{18}$-alkylene group and Me is Na or K.

Component iii) is in particular hexamethylene diisocyanate, isophorone diisocyanate, methyldiphenyl isocyanate (MDI) and/or tolylene diisocyanate.

The polyurethanes can be obtained in that the compounds from groups i) and ii) are reacted in an inert gas atmosphere in an inert solvent at temperatures from 70 to 130° C. with the compounds of group iii). This reaction can be optionally carried out in the presence of chain extenders, in order to produce polyurethanes with higher molecular weights. As usual in the production of polyurethanes, components [(i)+(ii)]:(iii) are advantageously used in a molar ratio of 0.8-1.1:1. The acid number of the polyurethanes is determined by the composition and the concentration of the compounds of the components (ii) in the mixture of the components (i)+(ii).

Following neutralization, the polyurethanes containing acid groups are (partially or completely) soluble in water or are dispersible without the aid of emulsifiers. Generally, the salts of the polyurethanes have better solubility in water or dispersibility in water than the non-neutralized polyurethanes. Bases which can be used for the neutralization of the polyurethanes are alkali metal bases, such as sodium hydroxide solution, potassium hydroxide solution, sodium carbonate, sodium bicarbonate, potassium carbonate or potassium bicarbonate, and alkaline earth metal bases, such as calcium hydroxide, calcium oxide, magnesium hydroxide or magnesium carbonate, and ammonia and amines. 2-Amino-2-methylpropanol, diethylaminopropylamine and triisopropanolamine have proven particularly useful for the neutralization of polyurethanes which contain acid groups. The neutralization of the polyurethanes which contain acid groups can also be carried out using mixtures of two or more bases, e.g. mixtures of sodium hydroxide solution and triisopropanolamine. Depending on the intended use, the neutralization can be partial, e.g. to an extent of 20 to 40%, or complete, i.e. to an extent of 100%.

These polymers and their preparation are described in more detail in DE-A-42 25 045, to the entire scope of which reference is made here.

Water-soluble or water-dispersible, cationic polyurethanes and polyureas can be produced from
a) at least one diisocyanate, which may already have been reacted beforehand with one or more compounds which contain two or more active hydrogen atoms per molecule, and
b) at least one diol, primary or secondary aminoalcohol, primary or secondary diamine or primary or secondary triamine having one or more tertiary, quaternary or protonated tertiary amino nitrogen atoms.

Preferred diisocyanates are those given above. Compounds having two or more active hydrogen atoms are diols, aminoalcohols, diamines, polyesterols, polyamidodiamines and polyetherols.

The polyurethanes are prepared as described above. Charged cationic groups can be generated in the polyureas from the present tertiary amino nitrogen atoms either by protonation, e.g. with carboxylic acids such as lactic acid, or by quaternization, e.g. using alkylating agents such as $C_1$- to $C_4$-alkyl halides or -sulfates. Examples of such alkylating agents are ethyl chloride, ethyl bromide, methyl chloride, methyl bromide, dimethyl sulfate and diethyl sulfate.

These polymers and their preparation are described in more detail in DE-A-42 41 118, to the entire contents of which reference is hereby made.

Linear polyurethanes having carboxylate groups can be produced from
i) a 2,2-hydroxymethyl-substituted carboxylic acid of the formula

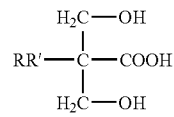

in which RR is a hydrogen atom or a $C_1$-$C_{20}$-alkyl group, which is used in an amount which is sufficient for 0.35 to 2.25 milliequivalents of carboxyl groups per g of polyurethane to be present in the polyurethane, ii) 10 to 90% by weight, based on the weight of the polyurethane, of one or more organic compounds having no more than two active hydrogen atoms and iii) one or more organic diisocyanates.

The carboxyl groups present in the polyurethane are, finally, at least partially neutralized with a suitable base. These polymers and their preparation are described in EP-A-619 111, to the entire contents of which reference is hereby made.

Also preferred are carboxyl-containing polycondensation products from anhydrides of tri- or tetracarboxylic acids and diols, diamines or aminoalcohols (polyesters, polyamides or polyester amides). These polymers and their preparation are described in more detail in DE-A-42 24 761, to the entire contents of which reference is hereby made.

Polyacrylates and polymethacrylates, as are described in more detail in DE-A-43 14 305, 36 27 970 and 29 17 504, are also preferred. Reference is hereby made to these publications in their entirety.

The polymers used according to the invention preferably have a K value of 25-100, preferably 25-50. The polymers are contained in the preparation according to the invention in general in an amount in the range of 0.2-20%, based on the total weight of the preparation. The salt is used in an amount effective for improving the exchangeability of the polymers. The salt is generally used in a quantity of 0.02-10% by weight, preferably 0.05-5% by weight and in particular 0.1-3% by weight, based on the total weight of the preparation.

It is advantageous according to the invention to select the molar ratio of glycopyrronium bromide to one or more hydrocolloids from the range of 100:1 to 1:100, preferably 50:1 to 1:50, in particular preferably 20:1 to 1:20.

After all this it was surprising and not foreseeable that also active agent combinations of glycopyrronium bromide and cationic polymers, in particular one or more mono-, oligo- and/or polysaccharides or cosmetic preparations containing such active agent combinations, as well as the use of such active agent combinations as an active principle of cosmetic deodorants and antiperspirants, eliminate the disadvantages of the prior art.

According to the invention it is therefore possible to obtain preparations which are active in deodorizing and/or antiperspirant manner with greater efficiency than the individual substances would have suggested.

Suitable mono-, oligo- and/or polysaccharides or "carbohydrate derivatives" which abbreviated are also referred to as "carbohydrates," are sugar and compounds containing substituted sugar or sugar radicals The sugars also include in particular respectively the desoxy forms.

The following active agents with sugar structures are preferred:

1. Monosaccharides

Suitable monosaccharides are, e.g., tetroses, pentoses, hexoses and heptoses. Pentoses and hexoses are preferred. The ring structures include furanoses and pyranoses, D- as well as l-isomers are also included, as are α and β anomers. The desoxy forms are also suitable.

2. Disaccharides

Suitable disaccharides are, e.g., the disaccharides formed by binary linkages of the above monosaccharides. Bonding can take place as α or β glycosidic bond between the two subunits. Saccharose, maltose, lactobiose are preferred.

3. Oligosaccharides

Suitable oligosaccharides comprise several, e.g., 2-7 sugar units, preferably the sugars described under 1 and 2, in particular 2 to 4 units in the known bond forms produced by condensation and specified as above. Particularly preferred oligosaccharides are the trisaccharides in addition to the disaccharides.

4. Amino Sugars

Mono-, di- and oligosaccharides are suitable, in particular as described above, with one or more amino groups, which can be acylated, in particular acetylated. Ribosylamine, N-acetyl glucosamine and N-galactosylamine are preferred.

Furthermore, sugar esters of organic or inorganic acids are advantageously used, e.g., sugar phosphates, sugar esters with carboxylic acids or sulfated sugars, in particular esters of the sugars described above.

5. Preferred sugar esters of phosphorus acid are glucose-1-phosphate, fructose-1-phosphate, glucose-6-phosphate or mannose-6-phosphate.

6. Preferred esters of sugars and carboxylic acids are obtained, e.g., with carboxylic acids having a chain length of C1 to C24, e.g., cetearylglucoside (Seppic: Montanol 68); caprylyl/caprylglucoside (Seppic: Oramix CG-110); decylglucoside (Seppic: Oramix NS-10), but also in particular the sugar acetates, preferably of the aforementioned sugars.

7. The sugar ethers of sugars are also preferred, in particular of the aforementioned sugars, with alcohols having a chain length of C1 to C24, e.g., PlantarenR 1200 (Henkel) or PlantarenR 2000 (Henkel).

8. Furthermore, e.g., the reaction products of sugars with ethylene oxide and/or propylene oxide are suitable, preferably with the above sugars. E/O degrees from one to 40 ether units are suitable.

9. Glycolipids

Preferred glycolipids are glycosphingolipids, in particular ceramides, cerebrosides, gangliosides and sulfatides.

10. Polysaccharides (of Natural and Synthetic Origin)

The polysaccharides can be unbranched or branched and both the homopolysaccharides and the heteropolysaccharides, in each case in particular with such sugars as described above under 1. through 7., are suitable. Preferred polysaccharides are starch, glycogen, cellulose, dextran, tunicin, inulin, chitin, in particular chitosans, alginic acid and alginates, plant gums, body mucins, pectins, mannans, galactans, xylans, araban, polyoses, chondroitin sulfates, heparin, hyaluronic acid and glycosaminoglycans, hemicelluloses, substituted celluloses and substituted starch, in particular in each case the hydroxyalkyl-substituted polysaccharides.

Chitosan, as presented above, is particularly suitable.

The polysaccharides can comprise, for example, 4 to 1,000,000, in particular 10 to 100,000, monosaccharides. Preferably, in each case those chain lengths are selected which guarantee that the active agent is soluble in the respective preparation or can be incorporated into it.

The active agents according to the invention can be used individually. However, it is also possible to use two, three or more active agents together. In particular, monosaccharides and oligosaccharides can be combined, where in each case one saccharide, but also two or three or more sugars can be chosen. Together with the aforementioned sugars or combinations thereof, advantageously one polysaccharide or also several polysaccharides can be used.

The following combinations and preparations therewith and their uses are preferred. Preference is given to active agent combinations with at least three active agents, selected form the group containing aldopentoses and ketopentoses and
aldohexoses and ketohexoses and
aldoheptoses and ketoheptoses.

The specified sugars can also be present in particular in their desoxy form and in particular also in the form of the derivatives according to the invention. This also applies to the following preferred combinations.

Combinations are particularly preferred, in particular combinations of at least three active agents, containing at least one desoxy-sugar or at least one desoxy-sugar derivative or at least one disaccharide or at least one trisaccharide, where these can also be present in each case in the form of the derivatives according to the invention or also the desoxy form.

Furthermore combinations are preferred, in particular combinations of at least three active agents that contain fucose, where these can also be present in each case in the form of the derivatives according to the invention.

The following combinations a)-f) are particularly preferred:
a) fucose,
raffinose and
galactose
b) glucose-6-phosphate,
mannose-6-phosphate and
mannose
c) raffinose,
N-acetyl glucosamin, and
fucose
d) mannose,
rhanmose and
fucose
e) galactose,
N-acetylglucosamin, and
fucose
f) mannose,
raffinose and
galactose.

The respective individual components of the combinations and the combinations of two to be formed with respectively two components of the three active agents respectively of a combination of three, are also preferred.

One or more sugars from the group of sugar phosphates and/or the amino sugars and acetylamino sugars can be advantageously combined respectively with one sugar or several sugars from the group of monosaccharides and/or oliogosaccharides.

It is advantageous according to the invention to select the molar ratio of glycopyrronium bromide to mono-, oligo- and/or polysaccharides from the range of 100:1 to 1:100, preferably 50:1 to 1:50, in particular preferably 20:1 to 1:20.

According to the knowledge of the prior art it was surprising and not foreseeable that oleaginous preparations containing glycopyrronium bromide and one or more clay minerals, and the use of mixtures of glycopyrronium bromide and one or more silicates as active principle of oleaginous cosmetic deodorants and antiperspirants eliminate the disadvantages of the prior art.

It was surprising that the compositions according to the invention are not only suitable for cosmetic purposes, but furthermore more effective and gentler than the compositions of the prior art. It seems that the silicates prevent, or at least significantly reduce, the sedimentation of the glycopyrronium bromide in the oil phase of oleaginous preparations. The addition of silicates improves the antiperspirant effect of glycopyrronium bromide in a surprising and not foreseeable manner.

Silicates are understood to mean preferably modified phyllosilicates, clay minerals and/or silicic acids.

Silicates are salts and esters (silicic esters) of orthosilicic acid [$Si(OH)_4$] and condensation products thereof. Only approximate chemical formulae can be given for phyllosilicates since they have a large ion-exchange capability, and silicon can be replaced by aluminium, and this in turn can be replaced by magnesium, $Fe^{2+}$, $Fe^{3+}$, $Zn^{2+}$ and the like. The negative charge of the layers which may result is usually balanced by cations, in particular by $Na^+$ and $Ca^{2+}$ in interlayer positions.

Advantageous phyllosilicates are, for example, those whose greatest expansion direction in the unmodified and unswollen state has, on average, a length of less than 10 μm. For example, the average expansions of the modified phyllosilicate particles used can be 1000 nm×100 m×1 nm and below. The effective size of the modified phyllosilicate particles in a cosmetic or dermatological formulation naturally depends on the amount of intercalated substances.

Advantageous modified phyllosilicates in the context of the present invention are, for example, modified smectites. Smectites are always very finely particulate (in most cases <2 mm) three-layer clay minerals (2:1 phyllosilicates) which occur mainly as lamella-shaped, moss-like or spherical aggregates, in which a central layer of octahedrally coordinated cations is sandwiched by two layers of [$(Si,Al)O_4$] tetrahedra.

Advantageous modified smectites are, for example, modified montmorillonites. Montmorillonites are described by the approximate chemical formula $Al_2[(OH)_2/Si_4O_{10}] \cdot n\, H_2O$ or $Al_2O_3 \cdot 4\, SiO_2 \cdot H_2O \cdot n\, H_2O$, and are clay minerals belonging to the dioctahedral smectites.

Also particularly advantageous in the context of the present invention are, for example, modified hectorites. Hectorites belong to the smectites and have the approximate chemical formula $M^+_{0.3}(Mg_{2.7}Li_{0.3})[Si_4O_{10}(OH)_2]$, in which $M^+$ is in most cases $Na^+$.

Also advantageous in the context of the present invention are modified bentonites. Bentonites are clays and rocks which contain smectites, especially montmorillonite, as main minerals. The "crude" bentonites are either calcium bentonites (referred to in Great Britain as Fuller's earth) or sodium bentonites (also: Wyoming bentonites).

Modified phyllosilicates in the context of the present invention are phyllosilicates, in particular the phyllosilicate types already mentioned, whose organophilicity (also: lipophilicity) has been increased, for example by reaction with quaternary ammonium compounds. Such phyllosilicates are also referred to as organophilic phyllosilicates.

Particularly advantageous for the purposes of the present invention are the so-called bentones, i.e., organic derivatives of montmorillonites (or bentonites) and/or hectorites, which are prepared by ion-exchange reactions with alkylammonium bases.

Advantageous modified phyllosilicates for the purposes of the present invention are obtainable, for example, by reacting phyllosilicates with quaternium-18. Quaternium-18 is a mixture of quaternary ammonium chloride salts which are described by the following structural formula:

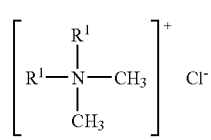

in which the radicals R1 are chosen independently of one another from hydrogenated tallow radicals having a chain length of from 12 to 20 carbon atoms.

According to the invention, particular preference is given to stearalkonium hectorite, a reaction product of hectorite and stearalkonium chloride (benzyldimethylstearyl-ammonium chloride), and quaternium-18 hectorite, a reaction product of hectorite and quaternium-18, which are available, for example, under the trade names Bentone 27 and Bentone 38 from Nordmann & Rassmann.

Quaternium-90 bentonite, a reaction product of bentonite and quaternium-90 that is available from Süd-Chemie under the trade name Tixogel VP-V, is likewise preferred according to the invention. The name indicates that the alkyl radicals R1 are of vegetable origin in this product, resulting in particularly advantageous properties in the context of the present invention and thickening of the matrix phase and reagitatability of the suspended antiperspirant active agent.

In the use of clay minerals, in addition a so-called activator can be used. This has the purpose of delaminating the clay mineral used, which is known as activating. Generally small polar molecules such as propylene glycolcarbonate and ethanol are used to this end, which insert themselves under mechanical energy input between the layers of the clay minerals, thus rendering possible the desired process through electrostatic interaction with them. Furthermore they form hydrogen bonds to the delaminated clay mineral flakes and through this bridge function—in a double function as clamp and hinge as it were—ensures the cohesion of the structure like a house of playing cards.

The described processes on a microscopic level cause a thickening of the liquid matrix and are reflected in an increase in the viscosity of the system that is easily observed macroscopically. These systems typically show a very marked thixotropy.

Silicic acids are compounds of the general formula $(SiO_2)_m \cdot n\, H_2O$. According to the invention, the pyrogenic silicic acids are very important. The term pyrogenic silicic acids covers highly dispersed silicic acids that are produced by flame hydrolysis (type A). Silicon tetrachloride is thereby decomposed in an oxyhydrogen flame:

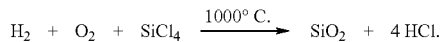

$$H_2 + O_2 + SiCl_4 \xrightarrow{1000^\circ C.} SiO_2 + 4\, HCl.$$

On their virtually pore-free surface they have far fewer OH groups than precipitation silicic acids. Because of their hydrophilicity due to the silanol groups, the synthetic silicic acids are frequently subjected to a chemical aftertreatment process, in which the OH groups react, e.g., with organic chlorosilanes. This results in modified, e.g., hydrophobic surfaces, which considerably expand the properties of the silicic acids in terms of application technology. They are available under the trade names Aerosil and Cab-O-Sil with different properties.

It is known to use silicates, as well as modified clays such as bentonites, is cosmetic formulas. Furthermore cosmetic deodorants are known with a content of such modified clays, e.g., EP-0 319 168. However, based on their chemical nature, these substances are completely unsuited to acting as deodorizing agents. They represent in the formulations of the prior art only auxiliaries or additives, which are designed to improve the consistency of the formulations or the like.

It has been proven that silicates can be successfully incorporated into all usual types of formulation of deodorants, e.g., in aerosols, powders, pump sprays, powder sprays, roll ons, deodorant sticks, tinctures and more.

Formulations with an active content of bentonites, smectites and silicic acids have proven to be particularly advantageous.

Furthermore, it can be advantageous to incorporate the usual cosmetic additives into the compositions, e.g., preservatives, antioxidants, photostabilizers, etc.

Otherwise, the usual measures for preparing cosmetic formulations are to be observed, with which one skilled in the art is familiar.

The silicates can be incorporated into the compositions according to the invention in a simple manner. They are preferably added to the other constituents as micronized particles, advantageous in the presence of a dispersant.

It is advantageous according to the invention to select the molar ratio of glycopyrronium bromide to one or more silicates from the range of 100:1 to 1:100, preferably 50:1 to 1:50, in particular 20:1 to 1:20.

Preferably the silicates are present in concentrations of 0.05-10.00% by weight. Particularly preferably the silicates are present in concentrations of 0.10-7.50% by weight, very particularly preferably in concentrations of 0.20-5.00% by weight. The concentrations given refer in each case to the total weight of the preparation.

An increase in the deodorizing/antiperspirant effect is observed in particular with the combinations according to the invention of GLYCOPYRROLATE and oils that are chosen from the group of alkyl benzoates, dialkyl carbonates and ethers, linear and/or branched-chain aliphatic hydrocarbons and/or short-chain hydrocarbon esters, in particular isopropyl esters.

The combination of glycopyrrolate with perfumes selected from the group of aldehydes, esters, ionones, methylionones, damascones, salicylates, acetals and/or wood bodies (Iso E Super) leads to an improved deodorizing effect. In order to minimize the negative effects of sweating, antiperspirant agents are used to reduce the sweat production by the axillae and deodorizing agents to prevent the development of unpleasant axillary odor. The decisive factor for the perception of the product effectiveness by the consumer thereby is the combination with a perfume that ensures a lasting pleasant axillary scent. The use of certain groups of perfumes that would be necessary for an optimal perfume has hitherto not been possible or possible only in insignificant quantities, since they cannot be used in a stable form in the presence of conventional antiperspirant agents.

It was surprisingly found that by replacing classic aluminum-based antiperspirant agents with glycopyrrolate, perfume ingredients can be incorporated in a stable manner which are important for optimizing the perfume, but which were previously ruled out for the prominent use. These prominent perfumes include in particular the chemical groups of aldehydes, esters, ionones and methyl ionones, damascones, salicylates, acetals and many wood bodies, especially Iso E Super.

It is particularly preferred to use glycopyrrolate in combination with perfumes selected from the group of aldehydes, here preferably lilial, hexylcinnamaldehyde-alpha, but also helional, citral, vertocitral, phenylacetaldehyde, esters, preferably linalyl acetate, terpenyl acetate, as well as dimethylbenzylcarbinylbutyrate, allylcaprylate, ionones, methylionones, damascones, salicylates, acetals and/or wood bodies, preferably Iso E Super, as well as Vertofix Coeur, Trimofix O in cosmetic preparations as an antiperspirant or a deodorant. Furthermore, using glycopyrrolate instead of the usual antiperspirant agents such as Al salts renders possible the stable incorporation of perfume ingredients. The use of aluminum-based antiperspirant agents is therefore preferably to be omitted, nevertheless achieving an antiperspirant or deodorant effect.

The use of glycopyrrolate instead of, e.g., aluminum chlorohydrate (ACH) in combination with one or more perfumes in a proportion of <1% by weight, in particular up to 0.5% by weight, based on the total mass of the cosmetic preparation, is preferred.

The listed perfume ingredients have been hitherto excluded for the prominent use and not used or used only in insignificant quantities, since they are not stable in the presence of classic antiperspirant agents. Through the use according to the invention of these perfume raw materials in deodorant/antiperspirant products, the scent of the perfume in the axillae is still perceptible long after application, achieving an additional deodorizing effect.

The combination of glycopyrrolate with phenoxyethanol causes an increase in the deodorant/antiperspirant effect. The hydrophilic glycopyrrolate in combination with the lipophilic phenoxyethanol means that glycopyrrolate remains in the oil phase of a cosmetic preparation, e.g., an emulsion. The lipophilic character of the skin therefore results in a better skin penetration by the glycopyrrolate, which in turn results in an increased effectiveness.

It was surprising and not foreseeable for one skilled in the art that a material that is suitable for application to the skin, containing glycopyrrolate in combination with antimicrobially active agentiferous glass of the composition

| | |
|---|---|
| $P_2O_5$ | 30-75 mol % |
| $SiO_2$ | 5-50 mol % |
| R1O | 20-55 mol % |
| $R2_2O$ | 0-5 mol % |
| $Al_2O_3$ | 3-20 mol % | based on the total quantity of the agentiferous glass, and 0.1-5% by weight of $Ag_2O$ based on the total mass of the glass where R1 is selected from Ca, Mg, Zn and/or Cu and R2 is selected from Na, K and/or Li, completely solves the bundle of problems.

The combination of glycopyrrolate with antimicrobially active glass of corresponding composition makes it possible to provide cosmetic preparations that in addition to the antiperspirant and antimicrobial effect are also aesthetically pleasing and above all gentle on the skin.

It is a particular advantage of the preparation according to the invention that the agentiferous glasses, in particular also through their advantageous dispersion, do not lead to any shortcomings compared to customary cosmetics. The advantage according to the invention lies in the storage stability and thus effectiveness over a longer period and in particular in the discoloration stability with respect to outside influences such as heat or sunlight. The preparations according to the invention thus do not exhibit any black or dark discoloration compared to other agentiferous cosmetics.

The specification of the glass composition in mol % refers to the constituents without silver oxide. In addition, the silver oxide quantity is given in % by weight based on the total mass of the then agentiferous glass.

In particular a material with a glass composition

| | |
|---|---|
| $P_2O_5$ | 40-60 mol %, |
| $R^1O$ | 35-55 mol %, |

-continued

| | |
|---|---|
| $R^2_2O$ | 0-5 mol %, |
| $SiO_2, Al_2O_3$ | 5-20 mol % and |
| $Ag_2O$ | 0.1-5% by weight and | a material with a glass composition

| | |
|---|---|
| $P_2O_5$ | 45-55 mol %, |
| CaO, MgO | 35-50 mol %, |
| $Na_2O, K_2O$ | 0-5 mol %, |
| $SiO_2$ | 0-5 mol %, |
| $Al_2O_3$ | 5-15 mol % and |
| $Ag_2O$ | 0.5-3% by weight | and preferably a material with a glass composition

| | |
|---|---|
| $P_2O_5$ | 50 mol %, |
| MgO | 44 mol %, |
| $Al_2O_3$ | 6 mol %, | based on the total quantity of the silver oxide-free glass and

| | |
|---|---|
| $Ag_2O$ | 2% by weight | based on the total mass of the glass, or with a glass composition

| | |
|---|---|
| $P_2O_5$ | 73.35% by weight, |
| MgO | 18.33% by weight, |
| $Al_2O_3$ | 6.32% by weight and |
| $Ag_2O$ | 2.0% by weight | based on the total glass mass, has proven to be particularly easy to apply and effective.

Ionpure A is a preferred agentiferous glass and a product of Ishizuka, J P. Likewise, C 1193 is a commercially available agentiferous glass.

FIG. 3 shows the reduction of the number of cells (*C. xerosis*) in preparations comprising glycopyrrolate and agentiferous glasses compared to preparations comprising only glycopyrrolate or agentiferous glasses (C-1193 or Ionpure A).

The synergism with respect to the reduction of the number of cells is noticeable here too.

Preparation or material according to the invention in this connection means everything that can be applied to human or animal skin and that can ensure the feeding and release of silver into the environment. These materials are in particular cosmetics, in particular cosmetic preparations on an emulsion-basis, disinfectant cleaning preparations and antimicrobially effective skin applications, pads or wipes.

These materials preferably contain 0.001-40% by weight, preferably 0.05-1% by weight of the agentiferous glass, based on the total weight of the material.

The silver with antimicrobial or disinfectant action is available in the form of free silver ions and designated as oxide $Ag_2O$ only according to the composition notation of the glass.

The preparations containing silver glass are generally emulsions or aqueous hydrogels which, besides customary humectants, can also comprise special active agents, such as, for example inflammation-alleviating and cooling substances,
local anaesthetic substances and/or
other active agents with cosmetic, pharmaceutical and/or dermatological action.

Use is made, for example, of inflammation-alleviating or -inhibiting active agents obtained from plants, such as azulene and bisabolol (camomile), glycyrrhizin (liquorice root), hamamelin (hamamelis) or entire extracts, e.g. from aloe vera or camomile. These display good successes in milder forms of inflammation and locally limited erythema reactions. The same is true for creams with a high content of essential oils or panthenol.

Due to the antimicrobial or disinfectant action of the silver glass, the preparations are used, i.a., for the prophylaxis and treatment of inflammatory skin conditions and/or to protect the skin.

It was surprising and not foreseeable to one skilled in the art that a water-in-silicone oil base for a clear antiperspirant oil comprising glycopyrrolate as active agent comprehensively solves the objects. The complete or partial replacement of aluminum salts by glycopyrrolate makes it possible to reduce the refractive index of the aqueous phase such that a much larger proportion of cost-effective silicone oils with lower refractive index can be incorporated in the silicone oil phase. This means that at the same time the stickiness of the products that is undesirable for sensory reasons is significantly reduced. Omitting aluminum salts is thus also preferred here as in the embodiments described above.

Through the larger selection for the silicone oil phase, at the same time the proportion of low-volatility silicone oils can also be increased, so that the cloudiness of the products after opening, which is undesirable for the consumer, is significantly reduced. The replacement of aluminum and aluminum zirconium salts by glycopyrrolate also facilitates the production of more transparent gels, since through the reduction or the omission of the aluminum salts often difficult to incorporate galenically, additional auxiliaries to adapt the refractive index of aqueous phase and oil phase can be used. In particular the replacement of highly volatile oils by low-volatility auxiliaries and oils thereby reduces the risk of cloudiness of the finished gel through evaporation of highly volatile constituents of the formula before or during the mixing of aqueous and oil phases.

It was also proven surprisingly and unforeseeably to one skilled in the art that glycopyrrolate in contrast to standard antiperspirant agents is also able from the internal phase to develop its antiperspirant effect without time delay and without performance restriction.

Another useful effect of the gels according to the invention is that through the replacement of the very acidic aluminum salts by glycopyrronium bromide, improved skin care properties are obtained.

Another advantage is that an oil phase with an increased proportion of silicone oils with lower refractive index leads to improved sensory properties.

According to the invention, antiperspirant preparations in transparent gel form based on O/W-PIT emulsions with a content of glycopyrronium bromide are preferred. It was surprising and not foreseeable for one skilled in the art that an oil-in-water base produced by means of PIT technology for a clear antiperspirant gel comprising glycopyrrolate as an active agent comprehensively solves the objects. The replacement of aluminum salts by glycopyrrolate provides greater freedoms in the choice of the emulsifier system, e.g., also the use of PEG-free emulsifiers, which in comparison exhibit an increased tolerance by the skin. Due to the omission of the highly cationic aluminum salts, moreover, lower amounts of associative thickeners can be used in order to achieve the same viscosity as with ACH-containing gels with higher contents of associative thickeners. Moreover, through the omission of ACH, other associative thickeners are available, the use of which must otherwise be omitted for stability reasons.

In this manner clear antiperspirant gels are obtained, which do not exhibit clouding through the evaporation of highly volatile oil components, even after opening, and which nevertheless in production provide greater form variability at lower cost than classic transparent PIT emulsions.

It was surprising and not foreseeable for one skilled in the art that through the replacement of the aluminum salts by glycopyrrolate, the PIT temperature shifts to lower temperatures. It is thus possible on the one hand to reduce energy costs in production, on the other hand still smaller droplet sizes can be set for the oil phase so that the gels become even more transparent.

Another useful effect of the gels according to the invention is that through the replacement of the highly acidic aluminum salts by glycopyrronium bromide, improved skin care properties are achieved.

The omission of aluminum-based antiperspirant active agents is thus as preferred as the omission of PEG, or to put it positively, the use of PEG-free emulsifiers.

According to the invention, antiperspirant preparations in stick form with advantageous sensory properties and reduced whitening effect are obtained through the combination of aqueous soap gel stick formulas with a content of glycopyrronium bromide.

Surprisingly and unexpectedly to one skilled in the art, an antiperspirant effect could be obtained from soap gel sticks without
  a negative effect on the gel structure of the stick through the addition of the antiperspirant agent
  or a negative effect on the antiperspirant effect of the antiperspirant agent due to the high pH value (around 10) of the soap gel stick.

Another useful effect of the gels according to the invention is that through the replacement of the highly acid aluminum salts by glycopyrronium bromide, a better skin care property is obtained.

It was surprisingly found that glycopyrrolate from surfactant-containing cleaning formulas develops a deodorant/antiperspirant effect even after cleansing the skin. This can be explained by the fact that the active mechanism of glycopyrrolate differs fundamentally from that of other antiperspirant agents. The sweat glands are not clogged, but deactivated.

Use in liquid or bar soaps is particularly advantageous. In combination with soaps, the classic antiperspirant agents form insoluble precipitates, which lead to clumping. This is not the case with glycopyrrolate.

Furthermore, the combination of glycopyrrolate with cationic polymers and/or lipophilic oils in surfactant-containing products is particularly advantageous, since they clearly improve the substantivity of the active agent and thus the effectiveness.

Soap Production:

The base soap noodles are fed into a conventional soap mixer (screw mixer with perforated screens) together with the dye slurry and the remaining components, homogenized by mixing several times, discharged through a plodder, cut and processed to form bars in the usual manner.

Consequently, it is also preferred here to omit the use of antiperspirant agents, in particular aluminum-containing antiperspirants, such as ACH.

As well as one or more oil phases, the cosmetic, pharmaceutical or dermatological formulations within the meaning of the present invention may preferably additionally comprise one or more water phases and be present, for example, in the form of W/O, O/W, W/O/W or O/W/O emulsions unless not preferably selected in form as above. Such formulations may preferably also be a microemulsion, a Pickering emulsion or a sprayable emulsion. In this case, plaster-like application forms can be impregnated with these emulsions.

According to the use according to the invention, the cosmetic preparations, in particular antiperspirants or deodorants, are particularly advantageously characterized in that the glycopyrronium bromide is present in concentrations of 0.01-10.00% by weight, preferably 0.05-5.00% by weight, particularly preferably 0.1-3.00% by weight, in each case based on the total weight of the preparation.

According to the use according to the invention, the preparations are particularly advantageously characterized in that the active agent(s) is/are present in each case independently of one another or in combination in a proportion of 0.01-10.00% by weight, preferably 0.05-5.00% by weight, particularly preferably 0.1-3.00% by weight, in each case based on the total weight of the preparation.

The active agent combinations can be preferably chosen by establishing the following weight ratios:

A:B:C) as a:b:c is chosen, where a, b and c, independently of one another, represent positive rational numbers from 1 to 200, preferably from 1 to 50 and A thereby represents the concentration of glycopyrronium bromide in weight units (e.g., % by weight), B thereby represents the concentration of an active agent, selected from the group of substances a.) through l.) in the same weight units, C thereby represents the concentration of a second active agent, selected from the group of substances a.) through l.), preferably selected from the group of substance B, in the same weight units, in each case based on the total weight of the preparation.

Thus, for example, polyethylene glycol(2)stearyl ether is chosen as component B and polyethylene glycol(21)stearyl ether as component C.

An active agent combination is then preferred in which the quotient (B+C)/A is selected from the range between 0.5 and 200, preferably from the range between 1 and 50.

It has been proven according to the invention that the objects of the invention, in particular an improved antiperspirant and deodorant effect, improved skin care properties, better serving as a vehicle for cosmetic and medicinal/dermatological active agents, and/or better sensory properties, such as, e.g., ease of distribution on or absorption into the skin, are attained when glycopyrrolate in combination with one or more active agents a.)-l.) and/or formulated in the form of a W/Si emulsion, an O/W gel, a W/O emulsion, an aerosol, an anhydrous stick or soap gel stick is used.

According to the invention, thereby one, several or all of the above-mentioned active agents can be preferably contained in the cosmetic preparation.

Conventional deodorants can also advantageously be added to preparations according to the invention. The conventional cosmetic deodorants are based on different active principles. All active agents common for deodorants can advantageously be used, for example odor concealers, such as customary perfume constituents, odor absorbers, for example the phyllosilicates described in DE 40 09 347, of these in particular montmorillonite, kaolinite, illite, beidellite, nontronite, saponite, hectorite, bentonite, smectite, and also, for example, zinc salts of ricinoleic acid. Antibacterial agents are also suitable for incorporation into the emulsions according to the invention. Advantageous substances are, for example, 2,4,4',-trichloro-2'-hydroxydiphenyl ether (Irgasan), 1,6-di (4-chlorophenylbiguanido)hexane (chlorhexidine), 3,4,4'-trichlorocarbanilide, quaternary ammonium compounds, oil of cloves, mint oil, thyme oil, triethyl citrate, farnesol (3,7,11-trimethyl-2,6,10-dodecatrien-1-ol), and the active agents or active agent combinations described in DE 37 40 186, DE 39 38 140, DE 42 04 321, DE 42 29 707, DE 42 29 737, DE 42 37 081, DE 43 09 372, DE 43 24 219. Sodium bicarbonate can also be used advantageously.

The amount of deodorants (one or more compounds) in the preparations is preferably 0.01 to 10% by weight, particularly preferably 0.05-5% by weight, based on the total weight of the preparation.

In accordance with the use according to the present invention the cosmetic deodorants can be in the form of aerosols, that is to say preparations which can be sprayed from aerosol containers, squeeze bottles or by a pump device, or in the form of liquid compositions which can be applied by means of roll-on devices, as deo sticks and in the form of W/O or O/W emulsions, for example, creams or lotions, which can be applied from normal bottles and containers. The cosmetic deodorants can furthermore advantageously be in the form of deodorizing tinctures, deodorizing intimate cleansing compositions, deodorizing shampoos, deodorizing shower or bath formulations, deodorizing powders or deodorizing powder sprays.

Cosmetic preparations are preferred which contain glycopyrrolate in a proportion of 0.05-5.00% by weight, particularly preferably 0.1-3.00% by weight, based on the total mass of the preparation, in combination with only one of the active agents selected from the group a.) to l.).

Cosmetic preparations are preferred which contain glycopyrrolate in a proportion of 0.05-5.00% by weight, particularly preferably 0.1-3.00% by weight, based on the total mass of the preparation, in combination with two of the active agents selected from the group a.) to l.).

Particularly preferred hereby are preparations in the form of a W/Si emulsion, an O/W gel or a soap gel stick.

As can be seen in particular based on the examples and based on the effectiveness studies shown by way of example (FIGS. 1, 2 and 3), the use of the active agent combinations, glycopyrrolate and one or more active agents, leads to a synergistic increase in the antiperspirant and/or deodorant effect compared to preparations comprising only one of the combination partners.

In particular, the deodorant and/or antiperspirant effect and the simultaneous skin care property of the preparations according to the invention should be mentioned.

In the following examples, which show preferred preparations, the proportions given are percentages by weight based on the total mass of the preparations, unless stated otherwise.

Exemplary Formulas

Alkoholic Roll-ons - transparent

| | Example No. 1 | Example No. 2 | Example No. 3 |
|---|---|---|---|
| | % by weight | | |
| Alcohol denat. | 20.000 | 30.000 | 20.000 |
| Hydroxyethylcellulose | 0.400 | 0.300 | 0.400 |
| Polyethylenglycol 400 | 3.000 | 2.000 | 3.000 |
| Polyethylenglycol (2000) hydrogenated castor oil | 2.000 | 3.000 | 2.000 |
| Avocado oil | 0.500 | 0.100 | 0.500 |
| Glycopyrronium bromide | 0.05 | 0.3 | 0.5 |
| Perfume, antioxidants | q.s. | q.s. | q.s. |
| Water, ad | 100.000 | 100.000 | 100.000 |

Deodorant creams Macroemulsions

| | 4 | 5 | 6 | 7 | 8 | 9 | 10 | 11 |
|---|---|---|---|---|---|---|---|---|
| | % by weight | | | | | | | |
| Polyethylene glycol (21) stearyl ether | 2.000 | 1.500 | 1.000 | 2.500 | 2.000 | 1.000 | 3.000 | 1.500 |
| Polyethylene glycol (2) stearyl ether | 2.500 | 2.500 | 2.200 | 1.500 | 2.000 | 3.000 | 2.500 | 3.000 |
| Polypropylene glycol (15) stearyl ether | 3.000 | 4.000 | 4.000 | 3.000 | 3.000 | 3.000 | 3.000 | 3.000 |
| Coconut fatty acid-2-ethylhexyl ester | — | — | — | 1.000 | — | — | 1.000 | — |
| Na$_3$HEDTA (20% aqueous solution) | 1.500 | 1.500 | 1.500 | 1.500 | 1.500 | 1.500 | 1.500 | 1.500 |
| Avocado oil | 0.100 | 0.100 | 0.100 | 0.100 | 0.100 | 0.100 | 0.100 | 0.100 |
| Perfume, antioxidants | q.s. | q.s. | q.s. | q.s. | q.s. | q.s. | q.s. | q.s. |
| Glycopyrronium bromide | 0.05 | 0.3 | 0.1 | 0.5 | 0.01 | 0.4 | 0.2 | 0.5 |
| Water, ad | 100.000 | 100.000 | 100.000 | 100.000 | 100.000 | 100.000 | 100.000 | 100.00 |

| | Example No. 12 | Example No. 13 | Example No. 14 |
|---|---|---|---|
| | % by weight | | |
| Glycerol monostearate | 4.000 | 3.500 | 3.500 |
| Polyethylene glycol (2000) monostearate | 4.500 | 4.000 | 4.000 |
| Cetyl alcohol | 5.000 | 4.000 | 4.000 |
| Decamethylcyclopentasiloxane | 6.000 | — | — |
| Isohexadecans | — | 6.000 | 6.000 |
| Paraffin oil | 4.500 | 4.000 | 4.000 |
| Na$_3$HEDTA (20% aqueous solution) | 1.500 | 1.000 | 1.000 |
| Perfume, antioxidants | q.s. | q.s. | q.s. |
| Glycopyrronium bromide | 0.05 | 0.4 | 0.3 |
| Water, ad | 100.00 | 100.00 | 100.00 |

Exemplary Formula 15

O/W Emulsion

| Raw material (INCI) | % by weight |
|---|---|
| Polyglyceryl-3-methylglucosedistearate | 2.00 |
| Stearyl alcohol | 2.00 |
| C$_{12-15}$ Alkyl benzoate | 3.00 |
| Butylene glycol dicaprylate/dicaprate | 2.00 |
| Cyclometicone | 3.00 |
| Hydrogenated Polydecene | 2.00 |
| Dimethylpolysiloxane (Dimethicone) | 1.00 |

-continued

| Raw material (INCI) | % by weight |
|---|---|
| Petrolatum | 1.00 |
| TiO2 | 1.00 |
| Glycopyrronium bromide | 2.00 |
| Allantoin | 0.10 |
| Phenoxyethanol | 0.40 |
| Iodopropynylbutylcarbamate | 0.05 |
| p-Hydroxybenzoic acid alkylester (Paraben) | 0.20 |
| Xanthan Gum | 0.10 |
| Carbomer | 0.10 |
| Butylene glycol | 3.00 |

-continued

| Raw material (INCI) | % by weight |
|---|---|
| Additives (talc, BHT) | 0.50 |
| Perfume | q.s. |
| Water | ad 100 |

Exemplary Formula 16

| Raw material (INCI) | % by weight |
|---|---|
| Polyglyceryl-3-methylglucose distearate | 3.00 |
| Cetyl alcohol | 1.00 |
| Cyclometicone | 3.00 |
| Dicapryl ether | 2.00 |
| Paraffinum liquidum | 3.00 |
| Ethylenediaminetetraacetic acid trisodium | 0.10 |
| Ccarbomer | 0.10 |
| Hydroxypropyl methylcellulose | 0.3 |
| Glycopyrronium bromide | 0.50 |
| Aluminum chlorohydrate | 5.00 |
| Glycerin | 3.00 |
| NaOH | q.s. |
| Preservatives | q.s. |
| Perfume | q.s. |
| Water | ad 100 |

Exemplary Formula 17

| Raw material (INCI) | % by weight |
|---|---|
| Polyglyceryl-3-methylglucose distearate | 3.00 |
| Sorbitan stearate | 1.00 |
| $C_{12-15}$ Alkylbenzoate | 2.00 |
| Ethylhexyl coconut fatty acid ester | 5.00 |
| Octamethyltetrasiloxane (Cyclomethicone) | 5.00 |
| Polydecene | 1.00 |
| Glycopyrronium bromide | 1.00 |
| Tocopherol | 0.10 |
| EDTA | 0.20 |
| para-Hydroxybenzoic acid alkyl ester (Paraben) | 0.40 |
| Methylpropanediol | 3.00 |
| Ethanol, denatured | 2.00 |
| Xanthan gum | 0.2 |
| Carbomer | 0.1 |
| Glycerin | 5.00 |
| Fillers/additives (distarch phosphate, talc) | 2.00 |
| Perfume | q.s. |
| Water | ad 100 |

Exemplary Formula 18 O/W Emulsion

| Raw material (INCI) | % by weight |
|---|---|
| Glyceryl stearate citrate | 1.50 |
| Cetylstearyl alcohol | 1.00 |
| Caprylic/Capric Triglyceride | 1.00 |
| Dicaprylcarbonate | 2.00 |
| Dimethyl polysiloxane, cyclic (Dimethicone) | 4.00 |
| Carbopol | 0.15 |
| Acrylic acid/C10-30 Alkyl methacrylate-Copolymer | 0.25 |
| Dimethicone | 0.75 |
| Jojoba oil | 1.00 |
| Tocopheryl acetate | 0.75 |
| Glycerin | 10.00 |
| Ethanol | 1.00 |
| Glycopyrronium bromide | 1.50 |
| Fillers/Additives (distarch phosphate, BHT, talc, aluminum starch octenylsuccinate, cyclodextrin) | 1.00 |
| Perfume | q.s. |
| Preservatives | q.s. |
| Water | ad 100 | pH value adjusted to 6.0

Exemplary Formula 19 O/W Emulsion

| Raw material (INCI) | % by weight |
|---|---|
| Glyceryl stearate citrate | 3.00 |
| Stearyl alcohol | 1.00 |
| Caprylic/Capric triglyceride | 1.00 |
| Octyldodecanol | 1.00 |
| Dicaprylether | 1.00 |
| Glycopyrronium bromide | 0.50 |
| Aluminum chlorohydrate | 3.00 |
| Carbomer | 0.15 |
| Glycerin | 3.00 |
| Perfume, preservatives, dyes, antioxidants, etc. | q.s. |
| Water | Ad 100 | pH value adjusted to 5.5

Exemplary Formula 20 O/W Emulsion

| Raw material (INCI) | % by weight |
|---|---|
| Glyceryl stearate citrate | 3.00 |
| Cetylstearyl alcohol | 1.00 |
| Cyclometicone | 4.00 |
| Octyldodecanol | 1.00 |
| Dimethicone | 1.00 |
| Glycopyrronium bromide | 1.00 |
| Allantoin | 0.10 |
| Citric acid, sodium salt | 0.10 |
| Thanol, denatured | 3.00 |
| Aluminum zirconium chlorohydrate | 3.00 |
| Ammonium acryloyldimethyltaurate/VP Copolymer | 0.30 |
| Glycerin | 10.00 |
| Fillers (distarch phosphate, SiO2, talc,) | 0.1 |
| Perfume, preservatives, antioxidants, etc. | q.s. |
| Water | Ad 100 | pH value adjusted to 5.5

Exemplary Formula 21 O/W Emulsion

| Raw material (INCI) | % by weight |
|---|---|
| Glyceryl stearate citrate | 2.00 |
| Cetylalcohol | 1.00 |
| Cyclometicone | 3.00 |
| Jojoba oil | 0.30 |
| Paraffinium liquidum | 1.00 |

-continued

| Raw material (INCI) | % by weight |
|---|---|
| Glycopyrronium bromide | 1.00 |
| Chitosan | 0.50 |
| Glycerin | 3.00 |
| Serine | 0.10 |
| Tocopherol acetate | 1.00 |
| Xanthan gum | 0.10 |
| Perfume, preservatives, dyes, antioxidants, etc. | q.s. |
| Water | Ad 100 | pH value adjusted to 6.0

Example 22

| Transparent Microemulsion Roll-on | |
|---|---|
| Chemical name | % by weight |
| Glycerin monoisostearate | 1.00 |
| Polyoxyethylene(20) isostearyl ether | 3.00 |
| Di-n-Octylcarbonate | 3.00 |
| 2-Octyldodecanol | 2.00 |
| Glycerin | 3.00 |
| Jojoba oil | 0.10 |
| Glycopyrronium bromide | 1.00 |
| 2-Ethylhexyl glycerin ether | 0.50 |
| Chitosan | 0.50 |
| Perfume, antioxidants | q.s. |
| Water, ad | Ad 100 |

Example 23

| Translucent Microemulsion - Atomizer | |
|---|---|
| Chemical name | % by weight |
| Polyoxyethylene(20) cetylstearyl ether | 2.00 |
| Polyoxyethylene(12) cetylstearyl ether | 1.00 |
| Glycerin stearate | 2.50 |
| Cetylstearyl alcohol | 0.50 |
| Cetyl palmitate | 0.50 |
| Caprylic-capric acid ester | 4.00 |
| Di-n-octylether | 8.00 |
| Glycerin | 3.00 |
| Glycopyrronium bromide | 0.30 |
| Pentanediol | 2.50 |
| Perfume, antioxidants | q.s. |
| Water, ad | 100 |

Example 24

| Macroemulsion roll-on | |
|---|---|
| Chemical name | % by weight |
| Polyethyleneglycol(21) stearyl ether | 3.00 |
| Polyethyleneglycol(2) stearyl ether | 2.00 |
| Polypropyleneglycol(15) stearyl ether | 2.00 |

-continued

| Macroemulsion roll-on | |
|---|---|
| Chemical name | % by weight |
| EDTA | 0.10 |
| Avocado oil | 0.10 |
| Perfume, antioxidants | q.s. |
| 2-Ethylhexyl glycerin ether (octoxyglycerin) | 0.50 |
| Hexanediol | 3.00 |
| Glycopyrronium bromide | 0.50 |
| Aluminum chlorohydrate | 3.00 |
| Water, ad | 100 |

Example 25

| Macroemulsion Cream | |
|---|---|
| Chemical name | % by weight |
| Glycerin monostearate | 5.00 |
| Polyethyleneglycol(2000) monostearate | 2.00 |
| Stearyl alcohol | 3.00 |
| Cyclometicone | 4.00 |
| Paraffin oil | 6.00 |
| EDTA | 0.20 |
| Chitosan | 0.50 |
| Glycopyrronium bromide | 0.80 |
| 2-Methylpropanediol | 3.00 |
| 2-Ethylhexyl glycerin ether | 0.50 |
| Perfume, antioxidants | q.s. |
| Water, ad | 100 |

Example 26

| Alcoholic Solution - Roll-on | |
|---|---|
| Chemical name | % by weight |
| Alcohol denat. | 25.00 |
| Hydroxyethylcellulose | 0.50 |
| Polyethyleneglycol 400 | 5.00 |
| Polyethyleneglycol (2000) hydrogenated castor oil | 4.00 |
| *Maccadamia* oil | 0.20 |
| Glycopyrronium bromide | 0.30 |
| Pentanediol | 5.00 |
| 2-Ethylhexyl glycerin ether | 0.50 |
| Perfume, antioxidants | q.s. |
| Water, ad | 100 |

Example 27

| Aerosol spray type A | % by weight |
|---|---|
| 2-Octyldodecanol | 0.50 |
| 1,2-Propyleneglycol | 1.00 |
| 2-Butyloctanoic acid | 0.25 |
| Glycopyrronium bromide | 0.50 |
| Perfume | q.s. |
| Ethanol | ad 100.00 |

The liquid phase obtained by mixing the respective constituents is placed in an aerosol container with a propane/butane mixture (2.7) in a ratio of 39:61.

Example 28

| Aerosol spray type B | I % by weight | II % by weight |
|---|---|---|
| Aluminum chlorohydrate | 45.00 | 25.00 |
| Isopropyl palmitate | 25.00 | 30.00 |
| Cyclomethicone | ad 100.00 | 0.30 |
| Isoparaffin | — | ad 100.00 |
| Talc | — | 10.00 |
| 2-Hexyldecanoic acid | 0.25 | 0.30 |
| Glycopyrronium bromide | 0.50 | 0.20 |
| Perfume | q.s. | q.s. |

The liquid phase obtained by mixing the respective constituents is placed in an aerosol container with a propane/butane mixture (2.7) in a ratio of 17:83.

Exemplary Formula 29 O/W Emulsions

| Raw material (INCI) | % by weight |
|---|---|
| Glyceryl stearate citrate | 2.00 |
| Cetylstearyl alcohol | 2.00 |
| Cyclomeitcone | 3.00 |
| Caprylic acid/capric acid triglyceride | 4.00 |
| Octyldodecanol | 1.00 |
| Dimethicone | 2.00 |
| Glycopyrronium bromide | 0.50 |
| Citric acid, sodium salt | 0.10 |
| Ethanol denatured | 3.00 |
| Ammonium acryloyldimethyltaurate/VP copolymer | 0.30 |
| Glycerin | 3.00 |
| Fillers (distarch phosphate, talc) | 0.10 |
| Perfume/dyes | q.s. |
| Water | Ad.100 |

Exemplary Formula 30 O/W Emulsions

| Raw material (INCI) | % by weight |
|---|---|
| PEG-40-Stearate | 2.00 |
| Glyceryl stearate | 2.00 |
| Stearyl alcohol | 0.50 |
| Cetyl alcohol | 2.00 |
| C12-15 Alkylbenzoate | 2.00 |
| Caprylic acid/capric acid triglyceride | 1.00 |
| Cyclomethicone | 3.00 |
| Dicaprylyl carbonate | 2.00 |
| Glycopyrronium bromide | 0.75 |
| Tartaric acid, sodium salt | 0.10 |
| Phenoxyethanol | 0.40 |
| Diazolidinyl urea | 0.20 |
| Ethanol denatured | 8.00 |
| Ammonium acryloyldimethyltaurate/VP copolymer | 0.80 |
| Glycerin | 5.00 |
| Fillers (distarch phosphate, BHT, talc) | 0.10 |
| Perfume/dyes | q.s. |
| Water | Ad 100 |

Exemplary Formula 31 Microemulsions

| Raw material (INCI) | % by weight |
|---|---|
| Lecithin | 1.00 |
| Oleth-15 | 5.00 |
| Phenoxyethanol | 0.50 |
| Hexamidinyl urea | 0.10 |
| Iodopropynyl butylcarbamate | 0.25 |
| Acrylates/$C_{10-30}$ Alkyl Acrylate Crosspolymer | 0.30 |
| Polyurethane-4 (Avalure UR-445) | 0.50 |
| Hydrophobized AMPS Copolymer | 0.20 |
| Glycopyrronium bromide | 1.00 |
| Aluminum chlorohydrate | |
| Glycerin | 6.00 |
| Perfume | q.s. |
| Fillers (distarch phosphate, $SiO_2$, talc, aluminum stearate | q.s. |
| Water | ad 100 |

Exemplary Formula 32 Microemulsions

| Raw material (INCI) | % by weight |
|---|---|
| Lecithin | 1.00 |
| Oleth-15 | 5.00 |
| Phenoxyethanol | 0.50 |
| Hexamidinyl urea | 0.10 |
| Iodopropynyl butylcarbamate | 0.25 |
| Acrylates/$C_{10-30}$ Alkyl Acrylate Crosspolymer | 0.30 |
| Polyurethane-4 (Avalure UR-445) | 0.50 |
| Hydrophobized AMPS Copolymer | 0.20 |
| Glycopyrronium bromide | 1.00 |
| Glycerin | 6.00 |
| Perfume | q.s. |
| Fillers (distarch phosphate, $SiO_2$, talc, aluminum stearate | q.s. |
| Water | Ad 100 |

Exemplary Formula 33 Microemulsion

Roll on

| | % |
|---|---|
| Glycerin monoisostearate | 1.00 |
| Polyoxyethylene(20) isostearyl ether | 2.00 |
| Di-n-octylcarbonate | 3.00 |
| 2-Octyldodecanol | 1.00 |
| Panthenol | 1.00 |
| Jojoba oil | 0.10 |
| Hydrophobically modified hydroxyethylcellulose | 0.20 |
| Glycopyrronium bromide | 0.50 |
| 2-Phenoxyethanol | 0.50 |
| Perfume, antioxidants | q.s. |
| Water, ad | ad 100 |

Exemplary Formula 34 Translucent Microemulsion

Atomizer

|  | % |
|---|---|
| Polyoxyethylene(20) cetylstearyl ether | 2.00 |
| Polyoxyethylene(12) cetylstearyl ether | 1.00 |
| Glycerinstearate | 2.00 |
| Cetylstearyl alcohol | 0.50 |
| Cetyl palmitate | 0.50 |
| Caprylic-capric acid ester | 3.00 |
| Di-n-octylether | 7.00 |
| Glycerin | 3.00 |
| Carrageenan | 0.2 |
| Glycopyrronium bromide | 0.50 |
| 2-Phenoxyethanol | 0.50 |
| Perfume, antioxidants | q.s. |
| Water, ad | 100 |

Exemplary Formula 35 Macroemulsion

Roll On

| Chemical name | In % |
|---|---|
| Polyethyleneglycol(21) stearyl ether | 3.00 |
| Polyethyleneglycol(2) stearyl ether | 2.00 |
| Polypropyleneglycol(15) stearyl ether | 2.00 |
| EDTA | 0.1 |
| Acryloyldimethyl taurate | 0.4 |
| Macadamia oil | 0.10 |
| Perfume, antioxidants | q.s. |
| 2-Phenoxyethanol | 0.5 |
| Glycopyrronium bromide | 1.50 |
| Water, ad | 100 |

Example 36

| Pump atomizer | % by weight |
|---|---|
| Ethanol | 55.00 |
| PEG-40 hydrogenated castor oil | 2.00 |
| Glycerin | 1.00 |
| 2-Butyloctanoic acid | 0.20 |
| Glycopyrronium bromide | 0.60 |
| Perfume | q.s. |
| Water | ad 100.00 |

Example 37

| Roll-on Gel | I<br>% by weight | II<br>% by weight |
|---|---|---|
| Ethanol | 50.00 | 50.00 |
| PEG-40 hydrogenated castor oil | 2.00 | 2.00 |
| Hydroxyethylcellulose | 0.50 | 0.50 |
| 2-Butyloctanoic acid | 0.20 | 0.30 |
| Glycopyrronium bromide | 0.10 | 0.20 |
| Aluminum chlorohydrate | — | 10.00 |
| Perfume | q.s. | q.s. |
| Water | ad 100.00 | ad 100.00 |

Example 38

| Roll-on Emulsion: | I<br>% by weight | II<br>% by weight |
|---|---|---|
| Aluminum chlorohydrate | — | 10.00 |
| Polypropyleneglycol(15) stearyl ether | 5.00 | 5.00 |
| Polyethyleneglycol(100) stearyl ether | 1.00 | 1.00 |
| Polyethyleneglycol(2) stearyl ether | 4.00 | 4.00 |
| 2-Hexyldecanoic acid | 0.20 | 0.30 |
| Glycopyrronium bromide | 2.00 | 3.00 |
| Perfume, preservatives | q.s. | q.s. |
| Water | ad 100.00 | ad 100.00 |

Example 39

| Deodorant stick type A | I<br>% by weight | II<br>% by weight | III<br>% by weight |
|---|---|---|---|
| Sodium stearate | 7.00 | 7.00 | 7.00 |
| 1,2-Propyleneglycol | 48.00 | 48.00 | 48.00 |
| Glycopyrronium bromide | 0.20 | 0.30 | 0.30 |
| 2-Butyloctanoic acid | — | 0.10 | — |
| 2-Hexyldecanoic acid | 0.20 | — | — |
| Perfume, preservatives | q.s. | q.s. | q.s. |
| Water | ad 100.00 | ad 100.00 | ad 100.00 |

Example 40

| Deodorant stick type B | I<br>% by weight | II<br>% by weight | III<br>% by weight |
|---|---|---|---|
| Sodium stearate | 8.00 | 8.00 | 8.00 |
| 1,2-Propyleneglycol | 45.00 | 45.00 | 45.00 |
| Glycopyrronium bromide | 0.20 | 0.30 | 0.30 |
| 2-Butyloctanoic acid | — | 0.50 | — |
| 2-Hexyldecanoic acid | 0.50 | — | — |
| Polyethyleneglycol(25) cetearyl ether | 3.00 | 3.00 | 3.00 |
| Ethanol | 20.00 | 20.00 | 20.00 |
| Perfume, preservatives | q.s. | q.s. | q.s. |
| Water | ad 100.00 | ad 100.00 | ad 100.00 |

Example 41-43

Aerosol Sprays

| | Example No. | | |
|---|---|---|---|
| | 41 | 42 | 43 |
| | % by weight | | |
| Glycopyrronium bromide | 0.6 | 0.5 | 0.5 |
| Chitosan lactate | 0.5 | 0.3 | — |
| Cyclomethicone | 8.5 | — | 12.8 |
| $C_{12}$-$C_{15}$ Alkyl benzoate | 3.0 | 5.0 | — |
| Dicaprylyl carbonate | — | 2.0 | — |
| Isohexadecane | — | 9.1 | — |
| Polydimethylsiloxane | 0.9 | 1.0 | 2.0 |
| Disteardimonium hectorite | 0.6 | — | 0.4 |
| Silicon dioxide | — | 1.1 | 0.3 |
| Talc | — | — | 3.0 |
| Perfume | 0.9 | 1.0 | 1.0 |
| Propellant gas mixture | 85.0 | 80.0 | 80.0 |
| Total | 100.0 | 100.0 | 100.0 |

Examples 44-46

Sticks

| | Example No. | | |
|---|---|---|---|
| | 44 | 45 | 46 |
| | % by weight | | |
| Glycopyrronium bromide | 0.5 | 1.0 | 0.5 |
| Chitosan hydrochloride | 0.5 | 0.5 | — |
| Cyclomethicone | 51.0 | 45.0 | 45.2 |
| $C_{12}$-$C_{15}$ Alkylbenzoate | — | 15.0 | 10.0 |
| PPG-14 butyl ether | 15.0 | 5.0 | — |
| Polydimethylsiloxane | — | — | 10.0 |
| Disteardimonium hectorite | 1.0 | — | 1.0 |
| Silicon dioxide | — | 1.0 | 0.8 |
| Stearylalcohol | 20.0 | 20.0 | 18.0 |
| Hydrogenated castor oil | 1.0 | 1.5 | 1.5 |
| Talc | 10.0 | 10.0 | 12.0 |
| Perfume | — | 1.0 | 1.0 |
| Total | 100.0 | 100.0 | 100.0 |

Examples 47-48

Deodorant roll-on

| | Example No. | |
|---|---|---|
| | 47 | 48 |
| | % by weight | |
| Glycopyrronium bromide | 0.5 | 1.0 |
| Chitosan acetate | 0.3 | 0.4 |
| Cyclomethicone | 82.2 | 76.0 |
| $C_{12}$-$C_{15}$ Alkylbenzoate | 2.0 | 5.0 |
| Polyisobutene | 0.5 | 2.0 |
| Isohexadecane | 10.0 | 5.0 |
| Quaternium-90 bentonite | 2.5 | 2.8 |
| Mineral oil | — | 5.0 |
| Propylene carbonate | 0.5 | 0.8 |
| Water | 0.5 | 1.0 |
| Perfume | 1.0 | 1.0 |
| Total | 100.0 | 100.0 |

Example 49

Transparent Microemulsion - Roll-on

| Chemical name | In % |
|---|---|
| Glycerin monoisostearate | 2.00 |
| Polyoxyethylene(20) isostearyl ether | 4.00 |
| Di-n-octylcarbonate | 2.00 |
| 2-Octyldodecanol | 2.00 |
| Glycerin | 3.00 |
| Avocado oil | 0.10 |
| Glycopyrronium bromide | 0.05 |
| Chitosan | 0.50 |
| Lactic acid | 0.13 |
| Perfume, antioxidants | q.s. |
| Water, ad | ad 100 |

Example 50

Translucent Microemulsion - Atomizer

| Chemical name | In % |
|---|---|
| Polyoxyethylene(20) cetylstearyl ether | 3.00 |
| Polyoxyethylene(12) cetylstearyl ether | 0.50 |
| Glycerin stearate | 3.00 |
| Cetylstearyl alcohol | 0.50 |
| Cetyl palmitate | 0.50 |
| Caprylic-capric acid ester | 5.00 |
| Di-n-octylether | 5.00 |
| Glycerin | 4.00 |
| Glycopyrronium bromide | 0.15 |
| Chitosan lactate | 0.30 |
| Perfume, antioxidants | q.s. |
| Water, ad | 100 |

Example 51

Macroemulsion - Roll-on

| Chemical name | In % |
|---|---|
| Polyethyleneglycol(21) stearyl ether | 2.00 |
| Polyethyleneglycol(2) stearyl ether | 2.50 |
| Polypropyleneglycol(15) stearyl ether | 3.00 |

-continued

Macroemulsion - Roll-on

| Chemical name | In % |
|---|---|
| Trisodium salt of ethylenediamine tetraacetic acid (20% aqueous solution) | 1.50 |
| Avocado oil | 0.10 |
| Perfume, antioxidants | q.s. |
| Lactic acid | 0.1 |
| Chitosan | 0.5 |
| Glycopyrronium bromide | 0.25 |
| Water, ad | 100 |

Example 52

Alcoholic Solution - Roll-on

| Chemical name | In % |
|---|---|
| Alcohol denat. | 20.00 |
| Hydroxyethylcellulose | 0.40 |
| Polyethyleneglycol 400 | 3.00 |
| Polyethyleneglycol (2000) hydrogenated castor oil | 2.00 |
| Avocado oil | 0.50 |
| Glycopyrronium bromide | 0.05 |
| Chitosan hydrochloride | 0.2 |
| Perfume, antioxidants | q.s. |
| Water, ad | 100 |

Exemplary Formula 53 O/W Gel Cream

| Raw material (INCI) | % by weight |
|---|---|
| Glyceryl stearate citrate | 1.25 |
| Cetyl stearyl alcohol | 0.75 |
| Caprylic/capric triglyceride | 1.00 |
| Dicapryl carbonate | 2.00 |
| Dimethylpolysiloxane, cyclic (Dimethicone) | 4.00 |
| Carbopol | 0.15 |
| Acrylic acid/C10-30 Alkylmethacrylate Copolymer | 0.25 |
| Dimethicone | 0.75 |
| Jojoba oil | 1.00 |
| Myristyl myristate | 1.00 |
| Tocopheryl acetate | 0.75 |
| Glycerin | 10.00 |
| Ethanol | 1.00 |
| Chitosan lactate | 0.80 |
| Glycopyrronium bromide | 1.50 |
| Perfume | q.s. |
| Preservatives | q.s. |
| Water | ad 100 |

Exemplary Formula 54 O/W Emulsion

| Raw material (INCI) | % by weight |
|---|---|
| Glyceryl stearate citrate | 3.00 |
| Stearyl alcohol | 1.00 |
| Caprylic/capric triglyceride | 1.00 |
| Octyldodecanol | 1.00 |
| Dicapryl ether | 1.00 |

-continued

| Raw material (INCI) | % by weight |
|---|---|
| Lactic acid | 0.08 |
| Chitosan | 0.30 |
| Glycopyrronium bromide | 0.50 |
| Carbomer | 0.15 |
| Glycerin | 3.00 |
| Perfume, preservatives, dyes, antioxidants, etc. | q.s. |
| Water | Ad 100 | pH value adjusted to 5.5

Exemplary Formula 55 O/W Emulsion

| Raw material (INCI) | % by weight |
|---|---|
| Polyglyceryl-3-methylglucose distearate | 3.00 |
| Stearyl alcohol | 3.00 |
| $C_{12-15}$ Alkylbenzoate | 3.00 |
| Butyleneglycol dicaprylate/dicaprate | 2.00 |
| Caprylic acid/capric acid triglyceride | 3.00 |
| Hydrogenated Polydecene | 2.00 |
| Dimethylpolysiloxane (Dimethicone) | 1.00 |
| Lactic acid | 0.25 |
| Chitosan | 1.00 |
| Glycopyrronium bromide | 2.00 |
| Sodium ascorbyl phosphate | 0.10 |
| Phenoxyethanol | 0.40 |
| Iodopropynyl butylcarbamate | 0.05 |
| p-Hydroxybenzoic acid alkyl ester (Paraben) | 0.20 |
| Xanthan Gum | 0.10 |
| Carbomer | 0.10 |
| Butylene glycol | 2.00 |
| Additives (Talc, BHT) | 0.50 |
| Perfume | q.s. |
| Water | ad 100 |

Exemplary Formula 56 O/W Emulsions

| Raw material (INCI) | % by weight |
|---|---|
| PEG-40-Stearate | 2.00 |
| Glyceryl stearate | 2.00 |
| Stearyl alcohol | 0.50 |
| Cetyl alcohol | 2.00 |
| C12-15 Alkylbenzoate | 2.00 |
| Caprylic acid/capric acid triglyceride | 1.00 |
| Cyclomethicone | 3.00 |
| Dicaprylyl carbonate | 2.00 |
| Lactic acid | 0.25 |
| Chitosan | 1.00 |
| Glycopyrronium bromide | 0.75 |
| Tartaric acid, sodium salt | 0.10 |
| Phenoxyethanol | 0.40 |
| Diazolidinyl urea | 0.20 |
| Ethanol denatured | 8.00 |
| Ammonium acryloyldimethyltaurate/VP copolymer | 0.80 |
| Glycerin | 5.00 |
| Fillers (distarch phosphate, $SiO_2$, talc, aluminum stearate) | 0.10 |
| Perfume/dyes | q.s. |
| Water | ad 100 |

Exemplary Formula 57 Microemulsions

| Raw material (INCI) | % by weight |
|---|---|
| Lecithin | 1.00 |
| Oleth-15 | 5.00 |
| Phenoxyethanol | 0.50 |
| Hexamidinyl urea | 0.10 |
| Iodopropynyl butylcarbamate | 0.25 |
| Xanthan gum | 0.10 |
| Polyurethane-4 (Avalure UR-445) | 0.50 |
| Hydrophobized AMPS Copolymer | 0.20 |
| Chitosan | 0.30 |
| Lactic acid | 0.08 |
| Glycopyrronium bromide | 1.00 |
| Glycerin | 6.00 |
| Perfume | q.s. |
| Fillers (distarch phosphate, $SiO_2$, talc, aluminum stearate | q.s. |
| Water | ad 100 |

Examples 58-60

Aerosol Sprays

| | Example No. | | |
|---|---|---|---|
| | 58 | 59 | 60 |
| | % by weight | | |
| Glycopyrronium bromide | 0.6 | 0.5 | 0.5 |
| Cyclomethicone | 9.0 | — | 12.8 |
| $C_{12}$-$C_{15}$ Alkylbenzoate | 3.0 | 5.0 | — |
| Dicaprylyl carbonate | — | 2.0 | — |
| Isohexadecane | — | 9.4 | — |
| Polydimethylsiloxane | 0.9 | 1.0 | 2.0 |
| Disteardimonium hectorite | 0.6 | — | 0.4 |
| Silicon dioxide | — | 1.1 | 0.3 |
| Talc | — | — | 3.0 |
| Perfume | 0.9 | 1.0 | 1.0 |
| Propellant gas mixture | 85.0 | 80.0 | 80.0 |
| Total | 100.0 | 100.0 | 100.0 |

Examples 61 to 63

Sticks

| | Example | | |
|---|---|---|---|
| | 61 | 62 | 63 |
| | % by weight | | |
| Glycopyrronium bromide | 0.5 | 1.0 | 0.5 |
| Cyclomethicone | 51.5 | 45.5 | 45.5 |
| $C_{12}$-$C_{15}$ Alkylbenzoate | — | 15.0 | 10.0 |
| PPG-14 butyl ether | 15.0 | 5.0 | — |
| Polydimethylsiloxane | — | — | 10.0 |
| Disteardimonium hectorite | 1.0 | — | 1.0 |
| Silicon dioxide | — | 1.0 | 0.5 |
| Stearylalcohol | 20.0 | 20.0 | 18.0 |
| Hydrogenated castor oil | 1.0 | 1.5 | 1.5 |
| Talc | 10.0 | 10.0 | 12.0 |
| Perfume | 1.0 | 1.0 | 1.0 |
| Total | 100.0 | 100.0 | 100.0 |

Examples 64 and 65

Deodorant Roll-ons

| | Example | |
|---|---|---|
| | 64 | 65 |
| | % by weight | |
| Glycopyrronium bromide | 0.5 | 1.0 |
| Cyclomethicone | 82.5 | 76.4 |
| $C_{12}$-$C_{15}$ Alkylbenzoate | 2.0 | 5.0 |
| Polyisobutene | 0.5 | 2.0 |
| Isohexadecane | 10.0 | 5.0 |
| Quaternium-90 bentonite | 2.5 | 2.8 |
| Mineral oil | | 5.0 |
| Propylene carbonate | 0.5 | 0.8 |
| Water | 0.5 | 1.0 |
| Perfume | 1.0 | 1.0 |
| Total | 100.0 | 100.0 |

Examples 66-70

Skin Cleansing Gels

| | 66 | 67 | 68 | 69 | 70 |
|---|---|---|---|---|---|
| Sodium laureth sulfate | 13.2 | 11 | 9.5 | 11 | 9.5 |
| Cocoamidopropyl betaine | 1.65 | 3.3 | 3.8 | 3.3 | 3.8 |
| PEG-7 Glyceryl cocoate | — | — | — | 2.0 | 2.0 |
| Laureth-2 | — | — | — | 0.1 | — |
| PEG-90 Glyceryl isosterate | — | — | — | 0.3 | — |
| Sodium cocoyl glutamate | 1.25 | 0.75 | 2.5 | 0.75 | 0.75 |
| PEG-40 hydrogenated castor oil | 0.50 | 0.50 | 0.5 | 0.50 | 0.50 |
| PEG-100 hydrogenated glyceryl palmitate | 0.50 | 0.50 | 0.5 | 0.50 | 0.50 |
| Glycopyrrolate | 0.025 | 0.025 | 0.05 | 0.02 | 0.1 |
| Polyquaternium-10 | 0.2 | — | 0.2 | — | — |
| Sodium benzoate | 0.45 | 0.45 | 0.45 | 0.45 | 0.45 |
| Sodium salicylate | 0.20 | 0.20 | 0.2 | 0.20 | 0.20 |
| Citric acid | 0.50 | 0.50 | 0.5 | 0.50 | 0.50 |
| Perfume | q.s. | q.s. | q.s. | q.s. | q.s. |
| Water | ad 100 | ad 100 | ad 100 | ad 100 | ad 100 |

Examples 71-73

LES-Free Skin Cleansing Gels

| | 71 | 72 | 73 |
|---|---|---|---|
| Sodium myreth sulfate | 5 | 4 | 6 |
| Lauryl glucoside | 2.5 | — | — |
| Decyl glucoside | — | 3 | — |
| Sodium cocoamphoacetate | 6.5 | 7 | 8 |
| PEG-200 hydrogenated glyceryl palmitate | 0.4 | 0.4 | 0.4 |
| PEG-40 hydrogenated castor oil | 1 | 1 | 1 |
| Diammonium citrate | 0.12 | 0.12 | 0.12 |
| Polyquaternium-10 | 0.2 | — | — |
| Glycopyrrolate | 0.025 | 0.025 | 0.05 |
| Sodium benzoate | 0.3 | 0.3 | 0.3 |
| Sodium salicylate | 0.2 | 0.2 | 0.2 |
| Citric acid | 1.2 | 1.2 | 1.2 |

|  | 71 | 72 | 73 |
|---|---|---|---|
| Perfume | q.s. | q.s. | q.s. |
| Water | ad 100 | ad 100 | ad 100 |

Examples 74-83

Face and/or Foot Cleansing Gels

|  | 74 | 75 | 76 | 77 | 78 |
|---|---|---|---|---|---|
| Sodium myreth sulfate | 2 | 4 | 3 | 5 | 2 |
| Decyl glucoside | 2 | 2 | 4 | 1 | 4 |
| Cocoamidopropyl betaine | — | 2 | — | 1 | 1 |
| Carbopol 1382 | 0.3 | 0.6 | 0.5 | 1 | — |
| Acrylates copolymer | 0.3 | 0.5 | 0.2 | 0.2 | 1 |
| Sodium hydroxide | 0.5 | 0.5 | 0.5 | 0.5 | 0.5 |
| Glycerin | 5 | 10 | 5 | 10 | — |
| $Na_3HEDTA$ | 0.5 | 0.5 | 0.5 | 0.5 | 0.5 |
| Glycopyrrolate | 0.025 | 0.5 | 0.025 | 0.05 | 0.01 |
| Phenoxyethanol | 0.5 | 0.5 | 0.5 | 0.5 | 0.5 |
| Parabene | 0.2 | 0.2 | 0.2 | 0.2 | 0.2 |
| Perfume | q.s. | q.s. | q.s. | q.s. | q.s. |
| Water | ad 100 | ad 100 | ad 100 | ad 100 | ad 100 |

|  | 79 | 80 | 81 | 82 | 83 |
|---|---|---|---|---|---|
| Sodium laureth sulfate | 2 | 2 | 7 | 7 | — |
| Methyl cocoyltaurate | 0.6 | 0.6 | 0.6 | 0.6 | 6 |
| Carbopol 980 | 1.2 | 1.2 | 1.2 | 0.5 | 0.6 |
| Sodium hydroxide | 0.5 | 0.5 | 0.5 | 0.5 | 0.5 |
| Glycerin | 2.0 | 2.0 | 2.0 | — | 2.0 |
| Glycopyrrolate | 0.025 | 0.025 | 0.5 | 0.5 | 0.01 |

-continued

| | | | | | |
|---|---|---|---|---|---|
| Xanthan gum | 0.25 | 0.1 | 0.25 | — | — |
| Phenoxyethanol | 0.5 | 0.5 | 0.5 | 0.5 | 0.5 |
| Paraben | 0.2 | 0.2 | 0.2 | 0.2 | 0.2 |
| Perfume | q.s. | q.s. | q.s. | q.s. | q.s. |
| Water | ad 100 | ad 100 | ad 100 | ad 100 | ad 100 |

Examples 84-88

Skin Cleansing Emulsions

|  | 84 | 85 | 86 | 87 | 88 |
|---|---|---|---|---|---|
| Paraffin oil | 46% | 14% | 20% | 20% | 25% |
| Soybean oil | 24.3% | 36% | 20% | 20% | 25% |
| Sodium lauryl ether sulfate | 7.35% | 12.3% | 11% | 11% | 11% |
| Sodium benzoate | 0.3% | 0.3% | 0.3% | — | 0.3% |
| Sodium salicylate | 0.2% | 0.2% | 0.2% | — | 0.2% |
| Acrylates/C10-C30 Alkyl Acrylate Crosspolymer | — | — | 1% | 1% | 0.8% |
| Glycopyrrolate | 0.025% | 0.025% | 0.05% | 0.02% | 0.1% |
| Sodium hydroxide | — | — | 0.2% | 0.2% | 0.2% |
| Phenoxyethanol | — | — | — | 0.5% | — |
| Parabens | — | — | — | 0.2% | — |
| Perfume | q.s. | q.s. | q.s. | q.s. | q.s. |
| Water | ad 100 | ad 100 | ad 100 | ad 100 | ad 100 |

Examples 89-101

Skin Cleansing Oils

| Raw material | 89 | 90 | 91 | 92 | 93 | 94 |
|---|---|---|---|---|---|---|
| Soybean oil | 34.0 | 35.0 | 5.0 | 40.0 | 45.0 | 35.5 |
| Mineral oil | 37.0 | 40.0 | 64.0 | 0.0 | 0.0 | 31.0 |
| Castor oil | 2.5 | 3.0 | 2.5 | 14.5 | 15.0 | 2.0 |
| Almond oil | 0.0 | 0.5 | 1.0 | 0.0 | 2.5 | 0.0 |
| Rice oil | 0.0 | 2.0 | 0.0 | 0.0 | 10.0 | 0.0 |
| Glycereth-8 rice oil | 0.0 | 0.0 | 0.0 | 0.0 | 0.0 | 1.0 |
| Panthenol solution 75% | 0.0 | 3.5 | 0.0 | 0.0 | 0.0 | 0.0 |
| Isohexadecane | 8.0 | 0.0 | 8.0 | 0.0 | 0.0 | 7.5 |
| MIPA-Laureth-sulfate | 2.5 | 0.0 | 5.0 | 20.5 | 0.0 | 6.0 |
| TIPA-Laureth-sulfate | 0.0 | 2.5 | 0.0 | 0.0 | 15 | 0.0 |
| Ethanol | 0.0 | 0.0 | 0.0 | 0.0 | 0.0 | 0.0 |
| EDTA solution 25% | 0.0 | 0.0 | 0.0 | 0.0 | 1.0 | 0.0 |
| PEG-30 Dipolyhydroxy stearate | 0.0 | 0.0 | 0.0 | 0.0 | 0.0 | 0.0 |
| PEG-40 Sorbitan persiostearate | 0.0 | 0.0 | 0.0 | 0.0 | 0.0 | 0.0 |
| Polyglyceryl-3 diisostearate | 0.0 | 0.0 | 0.0 | 0.0 | 0.0 | 0.0 |
| Laureth-4 | 1.5 | 0.0 | 3.0 | 12.5 | 0.0 | 3.5 |
| Cocamide DEA | 4.0 | 4.5 | 2.0 | 8.0 | 5.0 | 2.5 |
| Plant extract | 0.0 | 0.5 | 0.0 | 0.0 | 0.0 | 0.0 |
| Perfume | 3.0 | 3.0 | 3.0 | 1.5 | 2.0 | 3.0 |
| Lanolin alcohol | 1.5 | 0.0 | 1.0 | 0.0 | 0.0 | 1.0 |
| Octyldodecanol | 5.0 | 4.5 | 5.0 | 0.0 | 0.0 | 4.5 |
| Benzophenone-3 | 0.5 | 0.0 | 0.0 | 0.5 | 0.0 | 0.0 |
| Poloxamer 101 | 0.0 | 0.0 | 0.0 | 2.0 | 2.0 | 0.0 |
| Sea salt | 0.0 | | | | | |

| Raw material | (cont.) | | | | | |
|---|---|---|---|---|---|---|
| solution 30% | | | | | | |
| Coconut acid | 0.0 | 0.0 | 0.0 | 0.0 | 2.0 | 2.0 |
| Glycopyrrolate | 0.1 | 0.15 | 0.025 | 0.1 | 0.5 | 0.1 |
| Dye | 0.01 | 0.01 | 0.005 | 0.005 | 0.01 | 0.005 |
| Water | 0.2 | 0.0 | 0.1 | 0.1 | 0.0 | 0.1 |
| Mineral oil | add. 100 | add. 100 | add. 100 | add. 100 | add. 100 | add. 100 |

| Raw material | 95 | 96 | 97 | 98 | 99 | 100 | 101 |
|---|---|---|---|---|---|---|---|
| Soybean oil | 30.0 | 25.5 | 15.0 | 20.0 | 35.0 | 5.0 | 0.0 |
| Mineral oil | 40.0 | 40.0 | 45.0 | 40.0 | 0.0 | 710.0 | 70.0 |
| Castor oil | 4.0 | 3.5 | 3.5 | 10.0 | 20.0 | 5.0 | 5.0 |
| Almond oil | 0.0 | 1.5 | 0.5 | 0.0 | 0.0 | 0.0 | 0.0 |
| Rice oil | 2.0 | 0.0 | 0.0 | 2.0 | 5.0 | 0.0 | 0.0 |
| Glycereth-8 rice oil | 0.0 | 2.0 | 5.0 | 0.0 | 0.0 | 2.0 | 0.0 |
| Panthenol solution 75% | 0.0 | 3.0 | 0.0 | 3.0 | 0.0 | 0.0 | 0.0 |
| Isohexadecane | 7.0 | 6.0 | 6.0 | 5.0 | 5.0 | 0.0 | 0.0 |
| MIPA-Laureth-sulfate | 0.0 | 0.0 | 4.0 | 4.0 | 20.0 | 6.0 | 6.0 |
| TIPA-Laureth-sulfate | 5.0 | 4.5 | 0.0 | 0.0 | 0.0 | 0.0 | 0.0 |
| Ethanol | 0.5 | 1.0 | 0.0 | 0.0 | 0.0 | 0.0 | 0.0 |
| EDTA soluton 25% | 0.0 | 0.0 | 0.0 | 0.0 | 0.0 | 0.0 | 0.0 |
| PEG-30 Dipolyhydroxy stearate | 0.0 | 0.0 | 0.0 | 0.0 | 0.0 | 1.0 | 0.0 |
| PEG-40 Sorbitane persiostearate | 0.0 | 0.0 | 0.0 | 0.0 | 0.0 | 0.0 | 2.0 |
| Polyglyceryl-3 Diisostearate | 0.0 | 0.0 | 0.0 | 0.0 | 0.0 | 0.0 | 0.0 |
| Laureth-4 | 1.5 | 2.0 | 5.0 | 2.5 | 0.0 | 0.0 | 0.0 |
| Cocamide DEA | 2.5 | 3.0 | 0.0 | 0.0 | 3.0 | 4.0 | 6.0 |
| Plant extract | 0.5 | 0.0 | 0.0 | 1.0 | 0.0 | 0.0 | 1.0 |
| Perfume | 1.5 | 1.5 | 3.5 | 3.5 | 2.0 | 3.0 | 3.0 |
| Lanolin alcohol | 1.0 | 1.5 | 2.0 | 1.5 | 0.0 | 2.0 | 1.5 |
| Octyldodecanol | 4.0 | 3.5 | 3.5 | 3.0 | 3.0 | 0.0 | 3.0 |
| Benzophenone-3 | 0.0 | 0.5 | 0.0 | 0.0 | 0.5 | 0.0 | 0.0 |
| Poloxamer 101 | 0.0 | 0.0 | 0.0 | 1.5 | 2.0 | 0.0 | 2.0 |
| Sea salt solution 30% | 0.0 | 0.0 | 0.75 | 0.0 | 0.0 | 0.5 | 0.0 |
| Coconut acid | 0.0 | 0.0 | 0.0 | 0.0 | 3.0 | 0.0 | 0.0 |
| Glycopyrrolate | 0.05 | 0.05 | 0.1 | 0.5 | 0.2 | 0.1 | 0.05 |
| Dye | 0.01 | 0.01 | 0.01 | 0.01 | 0.005 | 0.005 | 0.01 |
| Water | 0.0 | 0.0 | 0.0 | 0.0 | 0.5 | 0.0 | 0.3 |
| Mineral oil | Add. 100 | Add. 100 | Add. 100 | Add. 100 | Add. 100 | Add. 100 | Add. 100 |

Examples 102-105

Pump Foamers

| | 102 | 103 | 104 | 105 |
|---|---|---|---|---|
| Sodium cocoyl glutamate | 2.5 | — | — | — |
| Sodium lauryl ether sulfate | — | 3.5 | — | — |
| Sodium lauroyl sarcosinate | — | — | 5 | — |
| Sodium myristyl ether sulfate | — | — | — | 4.5 |
| Decyl glucoside | 3 | 4 | — | — |
| Lauryl glucoside | — | — | 3 | 3 |
| Polyquaternium-10 | 0.1 | — | — | 0.1 |
| Guar hydroxypropyltrimonium chloride | — | 0.15 | — | — |
| Polyquaternium-22 | — | — | 0.2 | — |
| PEG-200 hydrogenated glyceryl palmitate | 0.5 | — | — | — |
| PEG-40 hydrogenated castor oil | 0.1 | 0.1 | 0.1 | 0.1 |
| PEG-100 hydrogenated glyceryl palmitate | — | 0.5 | — | 0.5 |
| Glycopyrrolate | 0.025 | 0.025 | 0.05 | 0.02 |
| Sodium benzoate | 0.5 | 0.5 | — | 0.5 |
| Sodium salicylate | — | 0.2 | — | 0.2 |
| Phenoxyethanol | — | — | 0.16 | — |
| Jojoba oil (*Buxus Chinensis*) | 0.1 | — | — | — |
| Citric acid | q.s. | q.s. | q.s. | q.s. |
| Perfume | q.s. | q.s. | q.s. | q.s. |
| Water | ad 100 | ad 100 | ad 100 | ad 100 |

Examples 106-110

Base Soaps

| | % by weight | % by weight | % by weight | % by weight | % by weight |
|---|---|---|---|---|---|
| Sodium tallowate | 68.0 | 68.0 | 65.0 | 0 | 68.0 |
| Sodium cocoate | 0 | 17.0 | 17.0 | 82.0 | 17.0 |
| Sodium palm | 17.0 | 0 | 0 | 0 | 0 |

-continued

|  | % by weight | % by weight | % by weight | % by weight | % by weight |
|---|---|---|---|---|---|
| kernel oil |  |  |  |  |  |
| Aqua | 11.0 | 11.0 | 12.0 | 12.0 | 11.0 |
| NaCl | 0.5 | 0.5 | 0.5 | 0.5 | 0.5 |
| EDTA | 0.2 | 0 | 0.2 | 0.2 | 0.2 |
| Sodium etidronate | 0.1 | 0.1 | 0 | 0.1 | 0.1 |
| Glycerin | 2.5 | 2.5 | 0.5 | 2.5 | 2.5 |
| Sodium palm kernel fatty acid salts | ad 100.0 | ad 100.0 | ad 100.0 | ad 100.0 | ad 100.0 |

Example 111-113

Dye Slurry

|  | % by weight | % by weight | % by weight |
|---|---|---|---|
| Wool wax alcohol | 2.0 | 15.0 | 0 |
| Paraffinum Liquidum | 33.0 | 45.0 | 33.0 |
| *Prunus Dulcis* | 45.0 | 0 | 30.0 |
| Disteardimonium hectorite | 1.0 | 3.0 | 1.0 |
| Dye | 0 | 1.5 | 0.5 |
| TiO$_2$ | 13.0 | 13.0 | 25.0 |
| Water | ad 100.0 | ad 100.0 | ad 100.0 |

Examples 114-116

Bar Soap

|  | % by weight | % by weight | % by weight | % by weight |
|---|---|---|---|---|
| Hydroxypropyl starch phosphate ester (Structure XL) | 1.0 | 0 | 0 | 0 |
| Dye slurry | 3.0 | 3.0 | 3.0 | 3.0 |
| Base soap | 85.0 | 86.8 | 85.9 | 91.0 |
| Paraffin | 1.5 | 1.0 | 1.0 | 2.0 |
| Polyethyleneglycol-150 | 0 | 0 | 0 | 2.0 |
| Talc | 7.0 | 9.0 | 0 | 6.0 |
| Glycopyrrolate | 0.1 | 0.05 | 0.15 | 0.025 |
| Perfume | 1.0 | 1.5 | 1.0 | 2.0 |
| Na$_2$S$_2$O$_3$ | 0.4 | 0.5 | 0.4 | 0.7 |
| Octyldodecanol | 0.5 | 0.5 | 0.5 | 0.5 |
| Water | ad 100.0 | ad 100.0 | ad 100.00 | ad 100.0 |

Examples 117-120

Combibar

|  | Gew.-% | Gew.-% | Gew.-% | Gew.-% |
|---|---|---|---|---|
| Hydroxypropyl starch phosphate ester (Structure XL) | 0 | 1 | 0 | 0 |
| Sodium cocoyl isetionate | 30.0 | 40.0 | 37.0 | 43.5 |
| Stearic acid | 22.7 | 22.5 | 22.2 | 22.7 |
| Base soap | 18 | 10 | 23 | 15 |
| Disodium lauryl sulfosuccinate | 17 | 9.5 | 9.5 | 12 |
| Talc | 0 | 10.0 | 5.0 | 5.0 |
| Coconut fatty acid | 3.5 | 3.3 | 3.3 | 3.8 |
| PEG-150 | 2.0 | 2.0 | 2.0 | 2.0 |
| Paraffin | 1.0 | 2.0 | 2.0 | 3.0 |
| TiO$_2$ | 0.5 | 0.5 | 0.5 | 0 |
| Panthenol | 0.5 | 0.3 | 1.0 | 0 |
| Glycopyrrolate | 0.1 | 0.05 | 0.2 | 0.025 |
| Lanolin Alcohol | 0.1 | 0.1 | 0 | 0.1 |
| Perfume | 1.0 | 1.5 | 2.0 | 1.5 |
| Water | ad 100.0 | ad 100.0 | ad 100.00 | ad 100.0 |

Examples 121-125

Syndets

|  | 121 | 122 | 123 | 124 | 125 |
|---|---|---|---|---|---|
| Hydroxypropyl starch phosphate ester (Structure XL) | 1 | 0 | 0 | 0 | 0 |
| Disodium lauryl sulfosuccinate | 15.0 | 30.0 | 21.0 | 21.0 | 13.0 |
| Sodium cocoyl isethionate | 20.0 | 15.0 | 21.0 | 15.0 | 34.0 |
| Cetearyl alcohol | 12.8 | 12.8 | 12.8 | 12.8 | 12.8 |
| Glyceryl Stearate | 12.0 | 12.0 | 12.0 | 12.0 | 12.0 |
| Paraffin | 11.8 | 11.8 | 11.8 | 14.0 | 11.8 |
| Wheat starch | 4.5 | 11.5 | 11.5 | 7.5 | 4.5 |
| Cocamidopropyl betaine | 2.0 | 2.0 | 2.0 | 2.0 | 2.0 |
| Citric acid | 1.5 | 1.5 | 1.5 | 2.0 | 1.5 |
| PEG-150 | 2.0 | 1.0 | 1.0 | 2.0 | 1.0 |
| Octyldodecanol | 3.0 | 0.0 | 0.5 | 0.5 | 3.0 |
| Jojoba oil | 0 | 1.0 | 0 | 0.5 | 0 |
| Talc | 3 | 0 | 0 | 0 | 0 |
| Dye | 0.5 | 1.0 | 0 | 0 | 0 |
| TiO$_2$ | 0.0 | 0.5 | 0.5 | 0.5 | 0.5 |
| Diammonium citrate | 0.1 | 0.1 | 0.1 | 0.5 | 0.1 |
| Lanolin alcohol | 0.1 | 0.1 | 0.1 | 0.1 | 0.0 |
| Glycopyrrolate | 0.3 | 0.05 | 0.15 | 0.025 | 0.1 |
| Perfume | q.s. | q.s. | q.s. | q.s. | q.s. |
| Water | ad 100 | ad 100 | ad 100 | ad 100 | ad 100 |

Examples 126-130

Liquid Soaps/Sweaty Hands Soap

|  | 126 | 127 | 128 | 129 | 130 |
|---|---|---|---|---|---|
| Sodium laureth sulfate | 5.0 | 4.5 | 5.0 | 5.0 | 10.5 |
| Sodium cocoamphoacetate | 5 | 5.5 | 0 | 5.0 | 0 |
| Cocoamidopropyl betaine | 0 | 0 | 4.5 | 0 | 4.5 |
| Natrium lauroyl sarcosinate | 0 | 0 | 0 | 0 | 1.6 |
| PEG-40 hydrogenated castor oil | 0.5 | 0.5 | 0.5 | 0.5 | 0.5 |
| PEG-7 Glyceryl cocoate | 1.0 | 1.5 | 0.75 | 1.0 | 0 |
| PEG-4 Rapeseed amide | 0 | 0 | 0 | 0 | 4.0 |
| PEG-9 Cocoglyceride | 0 | 0 | 0 | 0 | 1.6 |
| Glycerin | 1.5 | 1.0 | 2 | 1.5 | 0 |
| PEG-200 hydrogenated glyceryl palmitate | 0 | 0.5 | 0 | 0 | 1.5 |
| PEG-90 glyceryl isostearate | 0 | 0.5 | 0 | 0 | 0 |
| Laureth-2 | 0 | 0.1 | 0 | 0 | 0 |
| PEG-120 methylglucose | 0.5 | 0 | 0.3 | 0.5 | 0 |

-continued

|  | 126 | 127 | 128 | 129 | 130 |
|---|---|---|---|---|---|
| dioleate |  |  |  |  |  |
| Hydroxypropyl guarhydroxypropyl trimonium chloride | 0 | 0 | 0 | 0 | 0.3 |
| Sodium chloride | 0 | 0 | 0.2 | 0 | 0 |
| Trisodium EDTA | 0 | 0.2 | 0 | 0 | 0 |
| Tetrasodium iminodisuccinate | 0 | 0 | 1 | 0 | 0 |
| Polyquaternium-10 | 0.1 | 0 | 0 | 0.1 | 0 |
| Benzophenone-4 | 0 | 0.1 | 0 | 0 | 0 |
| Glycol distearate | 0 | 0 | 0.3 | 0 | 0 |
| Glycerin | 0 | 0 | 0.2 | 0 | 0 |
| Laureth-4 | 0 | 0 | 0.2 | 0 | 0 |
| Styrene/acrylate copolymer | 0 | 0 | 0 | 2.5 | 0 |
| Glycopyrrolate | 0.1 | 0.05 | 0.2 | 0.025 | 0.1 |
| Preservatives | q.s. | q.s. | q.s. | q.s. | q.s. |
| Dyes | q.s. | q.s. | q.s. | q.s. | q.s. |
| Citric acid | q.s. | q.s. | q.s. | q.s. | q.s. |
| Perfume | q.s. | q.s. | q.s. | q.s. | q.s. |
| Water | ad 100 | ad 100 | ad 100 | ad 100 | q.s. |

Examples 131-135

Afterfoaming Skin Cleansing Formulas

|  | 131 | 132 | 133 | 134 | 135 |
|---|---|---|---|---|---|
| Sodium laureth sulfate | 18.0 | 12.0 | 8.0 | 6.0 | 10.0 |
| Sorbit | 2.0 | 0 | 3.0 | 3.0 | 5.0 |
| Laureth-4 | 0 | 0 | 7.0 | 7 | 0 |
| Lanolin alcohol-PEG15 | 7.0 | 0 | 0 | 0 | 4.0 |
| Isopropyl palmitate | 0 | 0 | 3.0 | 3.0 | 5.0 |
| Isopropyl myristate | 4.0 | 2.0 | 0 | 0 | 0 |
| Glycerin | 0 | 5.0 | 2.0 | 1.0 | 0 |
| Xanthan gum | 0.5 | 0.5 | 0 | 0 | 0 |
| Phenoxyethanol | 0.2 | 0 | 0.2 | 0 | 0 |
| Parabens | 0.7 | 0 | 0.5 | 0 | 0 |
| Sodium hydroxide | 0.5 | 0 | 0.1 | 0.1 | 0 |
| Na₃HEDTA | 0.5 | 0 | 0.5 | 0 | 0 |
| Glycopyrrolate | 0.1 | 0.025 | 0.05 | 0.02 | 0.1 |
| Sodium benzoate | 0 | 0 | 0.0 | 0.5 | 0.5 |
| Citric acid | 0 | 0.2 | 0.5 | 0.5 | 0 |
| Polyquaternium-10 | 0 | 0 | 0.2 | 0.2 | 0.2 |
| Sodium salicylate | 0 | 0.5 | 0 | 0 | 0 |
| Dye | 0 | 0 | 0 | 0.5 | 0.3 |
| Gas/foaming agent | 10.0 | 5.0 | 12.0 | 9.0 | 7.0 |
| Perfume | q.s. | q.s. | q.s. | q.s. | q.s. |
| Water | ad 100 | ad 100 | ad 100 | ad 100 | ad 100 |

Examples 136-139

Soothing Baths and Footbaths

|  | 136 | 137 | 138 | 139 |
|---|---|---|---|---|
| Sodium laureth sulfate | 12.0 | 6.5 | 8.0 | 6.0 |
| Cocoamidopropyl betaine | 4.0 | 3.25 | 3.5 | 3.5 |
| Sodium cocoylglutamate | 0.5 | 0.2 | 0.5 | 0.5 |
| Decyl glucoside | 0.5 | 2.0 | 4.0 | 3.0 |
| PEG-40 hydrogenated castor oil | 0.5 | 0.5 | 0.5 | 0.5 |
| PEG-7 Glyceryl cocoate | 0.3 | 0.2 | 0.2 | 0.2 |
| Glycerin | 1 | 0 | 0 | 0.5 |
| Glyceryl laurate | 0.2 | 0 | 0 | 0 |
| PEG-200 hydrogenated glyceryl palmitate | 0.3 | 0.5 | 0 | 2.5 |

-continued

|  | 136 | 137 | 138 | 139 |
|---|---|---|---|---|
| PEG-90 glyceryl isostearate | 0 | 0 | 0.3 | 0.2 |
| Laureth-2 | 0 | 0 | 0.1 | 0.1 |
| PEG-120 methylglucose dioleate | 0 | 0.5 | 0 | 0 |
| Hydroxypropyl guarhydroxy-propyltrimonium chloride | 0 | 0 | 0.8 | 0 |
| Sodium chloride | 1.1 | 1.0 | 0 | 0.5 |
| Trisodium EDTA | 0 | 0 | 0 | 1.0 |
| Tetrasodium iminodisuccinate | 0.2 | 0 | 0 | 0 |
| Polyquaternium-10 | 0 | 0 | 0.5 | 0 |
| Benzophenone-4 | 0 | 0.1 | 0 | 0 |
| Glycol distearate | 0.8 | 0.6 | 0 | 0.6 |
| Glycerin | 0.4 | 0.3 | 0 | 0.3 |
| Laureth-4 | 0.4 | 0.3 | 0 | 0.3 |
| Styrene/acrylate copolymer | 0 | 0 | 1.0 | 0 |
| Plant extracts | 0 | 0.05 | 0 | 0 |
| Natural oils | 0 | 0 | 0 | 0.2 |
| Preservatives | q.s. | q.s. | q.s. | q.s. |
| Glycopyrrolate | 0.1 | 0.025 | 0.05 | 0.4 |
| Dyes | q.s. | q.s. | q.s. | q.s. |
| Citric acid | q.s. | q.s. | q.s. | q.s. |
| Perfume | q.s. | q.s. | q.s. | q.s. |
| Water | ad 100 | ad 100 | ad 100 | ad 100 |

All of the example compositions shown containing the active agent combination according to the invention of glycopyrrolate and at least one of the active agents selected from the group of active agents a. through l.) or in the form of a preparation m.), n.) or o.) as cosmetic or dermatological preparations, containing them,
  are characterized by better skin-care action,
  cause less stress to the biological balance of the skin due to skin neutrality,
  better serve as vehicles for cosmetic and medical/dermatological active agents,
  are characterized by better physiochemical stability of the formulas,
  are characterized by better biocompatibility,
  exhibit reduced stickiness on the skin,
  have better sensory properties, such as, e.g., being easily dispersed over the skin or easily absorbed by the skin,
than the active agents, active agent combinations and preparations of the prior art.

What is claimed is:

1. A cosmetic preparation, wherein the preparation comprises (i) glycopyrronium bromide and (ii) one or more dialkyl-substituted acetic acids.

2. The preparation of claim 1, wherein (ii) comprises one or more dialkyl-substituted acetic acids of formula

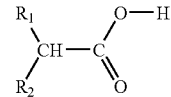

wherein:
  $R_1$ represents a branched or unbranched alkyl group having from 1 to 12 carbon atoms; and
  $R_2$ represents a branched or unbranched alkyl group having from 1 to 24 carbon atoms.

3. The preparation of claim 2, wherein $R_1$ is selected from methyl, ethyl, propyl, butyl, pentyl, and hexyl.

4. The preparation of claim 2, wherein $R_2$ is selected from octyl, nonyl, decyl, undecyl, and dodecyl.

5. The preparation of claim 3, wherein $R_2$ is selected from octyl, nonyl, decyl, undecyl, and dodecyl.

6. The preparation of claim 1, wherein (ii) comprises at least one of 2-butyl octanoic acid, 2-butyl decanoic acid, 2-hexyl octanoic acid, and 2-hexyl decanoic acid.

7. The preparation of claim 1, wherein a molar ratio (i):(ii) is from 100:1 to 1:100.

8. The preparation of claim 7, wherein the molar ratio is from 50:1 to 1:50.

9. The preparation of claim 8, wherein the molar ratio is from 20:1 to 1:20.

10. The preparation of claim 1, wherein the preparation comprises from 0.01% to 10.00% by weight of (i) and from 0.01% to 10.00% by weight of (ii), each based on a total weight of the preparation.

11. The preparation of claim 7, wherein the preparation comprises from 0.05% to 5.00% by weight of (i) and from 0.05% to 5.00% by weight of (ii), each based on a total weight of the preparation.

12. The preparation of claim 7, wherein the preparation comprises from 0.1% to 3.00% by weight of (i) and from 0.1% to 3.00% by weight of (ii), each based on a total weight of the preparation.

13. The preparation of claim 1, wherein the preparation is free of antiperspirant agents different from (i) and (ii).

14. The preparation of claim 1, wherein the preparation is free of aluminum-containing antiperspirants.

15. The preparation of claim 1, wherein the preparation is transparent.

16. The preparation of claim 1, wherein the preparation is present as a W/Si or O/W gel.

17. The preparation of claim 1, wherein the preparation is present as a liquid or bar soap, an aerosol, a deodorant stick, a cream, a lotion, a deodorizing tincture, a deodorizing feminine cleansing agent, a deodorizing shampoo, a deodorizing shower or bath preparation, a deodorizing powder, or a deodorizing powder spray.

18. The preparation of claim 1, wherein the preparation is present in association with at least one of an aerosol container, a squeeze bottle, a pump device and a roll-on device.

19. A cosmetic preparation, wherein the preparation comprises (i) glycopyrronium bromide and (ii) one or more dialkyl-substituted acetic acids which comprise at least one of 2-butyl octanoic acid, 2-butyl decanoic acid, 2-hexyl octanoic acid, and 2-hexyl decanoic acid, a molar ratio (i):(ii) being from 20:1 to 1:20.

20. The preparation of claim 19, wherein the preparation comprises from 0.05% to 5.00% by weight of (i), based on a total weight of the preparation.

21. The preparation of claim 20, wherein the preparation comprises from 0.05% to 5.00% by weight of (ii), based on a total weight of the preparation.

22. The preparation of claim 21, wherein the preparation comprises from 0.1% to 3.00% by weight of (i) and from 0.1% to 3.00% by weight of (ii).

23. The preparation of claim 19, wherein the preparation is free of aluminum-containing antiperspirants.

24. The preparation of claim 19, wherein (ii) comprises 2-butyl octanoic acid.

* * * * *